US005705621A

United States Patent [19]
Ravikumar

[11] Patent Number: 5,705,621
[45] Date of Patent: Jan. 6, 1998

[54] OLIGOMERIC PHOSPHITE, PHOSPHODIESTER, PHOSPHOROTHIOATE AND PHOSPHORODITHIOATE COMPOUNDS AND INTERMEDIATES FOR PREPARING SAME

[75] Inventor: Vasulinga T. Ravikumar, Carlsbad, Calif.

[73] Assignee: ISIS Pharmaceuticals, Inc., Carlsbad, Calif.

[21] Appl. No.: 560,540

[22] Filed: Nov. 17, 1995

[51] Int. Cl.$^6$ ............... C07H 21/00; C07F 9/02
[52] U.S. Cl. ............ 536/23.1; 536/22.1; 536/25.3; 536/25.31; 536/25.33; 536/25.34; 536/26.14; 536/26.7; 536/26.8; 558/70; 558/167; 558/168
[58] Field of Search ............... 536/22.1, 23.1, 536/25.3, 25.31, 25.33, 25.34, 26.14, 26.7, 26.8; 558/70, 167, 168

[56] References Cited

U.S. PATENT DOCUMENTS

| 34,069 | 9/1862 | Koster et al. . |
| 3,687,808 | 8/1972 | Merigan et al. . |
| 4,415,732 | 11/1983 | Caruthers et al. . |
| 4,458,066 | 7/1984 | Caruthers et al. . |
| 4,500,707 | 2/1985 | Caruthers et al. . |
| 4,668,777 | 5/1987 | Caruthers et al. . |
| 4,725,677 | 2/1988 | Koster et al. . |
| 4,816,571 | 3/1989 | Andrus et al. . |
| 4,973,679 | 11/1990 | Caruthers et al. . |
| 5,026,838 | 6/1991 | Nojiri et al . |
| 5,132,418 | 7/1992 | Caruthers et al. . |
| 5,210,264 | 5/1993 | Yau . |
| 5,212,295 | 5/1993 | Cook . |

FOREIGN PATENT DOCUMENTS

| 058 563 | 8/1982 | European Pat. Off. . |
| 090 789 | 10/1983 | European Pat. Off. . |
| 0 506 242 A1 | 9/1992 | European Pat. Off. . |
| WO 86/07362 | 12/1986 | WIPO . |
| WO 88/00201 | 1/1988 | WIPO . |
| WO 91/04983 | 4/1991 | WIPO . |

OTHER PUBLICATIONS

Alul, et al., "Oxalyl–CPG: a lablile support for synthesis of sensitive oligonucleotide derivatives" *Nucleic Acids Research*, 1991, 19, 1527–1532.

Bannwarth, W., "Synthesis of Oligodeoxynucleotides by the phosphite–triester method using dimer units and different phosphorous–protecting groups", *Helvetica Chimica Acta*, 1985, 69, 1907–1913.

Bielinska, A., et al., "Regulation of Gene Expression with Double–Stranded Phosphorothioate Oligonucleotides", *Science* 1990, 250, 997–1000.

Cook, P.D., "Medicinal Chemistry of Antisense Oligonucleotides", *Anti–Cancer Drug Design*, 1991, 6, 585–607.

Current Protocols in Molecular Biology, F.M., Ausubel, et al., Eds., Current Publications, 1993.

Beaucage, S.L. and Iyer, R.P., "Advances in the Synthesis of Oligonucleotides by the Phosphoramidite Approach", *Tetrahedron*, 1992, 48, 2223–2311.

Delgado, et al., "The Uses and Properties of PEG–Linked Proteins", *Critical Reviews in Therapeutic Drug Carrier Systems*, 1992, 9, 249–304.

Englisch, et al., "Chemically Modified Oligonucleotides as Probes and Inhibitors", *Angew. Chem. Int. Ed. Engl.*, 1991, 30, 613–722.

Greene and Wuts, *Protective Groups in Organic Synthesis*, Chapter 2, 2nd Ed., John Wiley & Sons, New York, 1991.

Iyer, R.P., et al., "3H–1, 2–benzodithiole–3–one 1,1–dioxide as an improved sulfurizing reagent in the solid–phase synthesis of oligodeoxyribonucleoside phosphorothioates", *J. Am. Chem. Soc.*, 1990, 112, 1253–1254.

Iyer, R.P., et al., "The Automated Synthesis of Sulfur–Containing Oligodeoxyribonucleotides Using 3H–1,2–Benzodithiol–3–one 1, 1–Dioxide as a Sulfur–Transfer Reagent", *J. Org. Chem.* 1990, 55, 4693–4699.

Kamer, P.C.J., et al., "An Efficient Approach Toward the Synthesis of Phosphorothiote Diesters Via the Schonberg Reaction" *Tetrahedron Letters*, 1989, 30, 6757–6760.

Kumar, G. and Poonian, M.S., "Improvements in oligodeoxyribonucleotide sunthesis: Methyl N, N–dialkylphosphoramidite dimer units for solid support phosphite methodology", *J. Org. Chem.* 1984, 49, 4905–4912.

*Concise Encyclopedia of Polymer Science and Engineering*, J.I., Kroschwitz, Ed., John Wiley & Sons, 1990, pp. 858–859.

1994–1995 Aldrich Chemical Company Catalog, p. 32.

Miura, K., et al., "Blockwise Mechanical Synthesis of Oligonucleotides by the Phosphoramidite Method", *Chem. Pharm. Bull.*, 1987, 35, 833–836.

Molecular Cloning, A Laboratory Manual, Second Ed., J. Sambrook, et al., Eds., Cold Spring Harbor Laboratory Press, 1989.

Oligonucleotides and Analogues, A Practical Approach, Ekstein, F., Ed., IRL Press, N.Y., 1991, Chapter 1, pp.1–23.

Ouchi, et al., "Synthesis and Antitumor Activity of Poly(ethylene Glycol)s Linked to 5–Fluorouracil Via a Urethane of Urea Bond", *Drug Design and Discovery*, 1992, 9, 93–105.

Ravasio, "Selective Hydrogenations Promoted by Copper Catalysts 1. Chemoselectivity, Regioselectivity, and Stereoselectivity in the Hydrogenation of 3–Substituted Steriods", *J. Org. Chem.* 1991, 56, 4329–4333.

Rao, et al., "Dibenzoyl Tetrasulphide–A Rapid Sulphur Transfer in the Syntheis of Phosphorothioate Analogues of Oligonucleotides", *Tetrahedron Letters*, 1992, 33 (33), 4839–4842.

Sanghvi, *Antisense Research and Application*, Crooke, S.T. and Lebleu, B., Eds., CRC Press, 1991.

(List continued on next page.)

Primary Examiner—James O. Wilson
Attorney, Agent, or Firm—Woodcock Washburn Kurtz Mackiewicz & Norris LLP

[57] ABSTRACT

Synthetic processes are provided wherein oligomeric compounds are prepared having phosphodiester, phosphorothioate, and phosphorodithioate covalent linkages. Also provided are synthetic intermediates useful in such processes.

28 Claims, No Drawings

OTHER PUBLICATIONS

Secrist, et al., Abstract 21, Program & Abstracts, Tenth International Roundtable, Nucleosides, Nucleotides and their Biological Applications, Park City, Utah, Sep. 16–20 1992.

Stec and Lesnikowski, *Methods in Molecular Biology*, vol. 20,: Protocols for Oligonucleotides and Analogs, S. Agrawal, Ed., Humana Press, Totawa, N.J. (1993), at Chapter 14, pp. 285–313.

Stec, et al., "Novel route to oligo (deoxyribonucleoside phosphorothioats). Stereocontrolled synthesis of P–chiral oligo (deoxyribonucleoside phosphorothioates)", *Nucleic Acid Research*, 1991, 19, 5883–5888.

Vu, et al., "Internucleotide Phosphate Sulfurization with Tetraethythiuram Disulfide, Phosphorothioate Oligonucleotide Synthesis via Phosphoramidite Chemistry", *Tetrahedron Letters*, 1991, 32, 3005–3008.

Wright, et al., "Large scale synthesis of oligonucleotides via phosphoramidite nucleosides and a high–loaded polystyrene support", *Tetrahedron Letters*, 1993, 34, 3373–3376.

Wolter, et al., "Polymer support oligonucleotide synthesis XX[1]: synthesis of a henhectacosa deoxynucleotide by use of a dimeric phoshormaidite sython", *Nucleosides & Nucleotides*, 1986, 5, 65–77.

Wu, et al., "Evidence for targeted gene delivery to hep g2 hepatoma cells in vitro", *Biochemistry*, 1988, 27, 887–892.

OLIGOMERIC PHOSPHITE, PHOSPHODIESTER, PHOSPHOROTHIOATE AND PHOSPHORODITHIOATE COMPOUNDS AND INTERMEDIATES FOR PREPARING SAME

FIELD OF THE INVENTION

This invention relates to methods for the preparation of oligomeric compounds having phosphite, phosphodiester, phosphorothioate, or phosphorodithioate linkages, and to intermediates useful in their preparation.

BACKGROUND OF THE INVENTION

Oligonucleotides and their analogs have been developed and used in molecular biology in certain procedures as probes, primers, linkers, adapters, and gene fragments. Modifications to oligonucleotides used in these procedures include labeling with nonisotopic labels, e.g. fluorescein, biotin, digoxigenin, alkaline phosphatase, or other reporter molecules. Other modifications have been made to the ribose phosphate backbone to increase the nuclease stability of the resulting analog. These modifications include use of methyl phosphonate, phosphorothioate, and phosphorodithioate linkages, and 2'-O-methyl ribose sugar units. Further modifications include those made to modulate uptake and cellular distribution. With the success of these compounds for both diagnostic and therapeutic uses, there exists an ongoing demand for improved oligonucleotides and their analogs.

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is a general object of such therapeutic approaches to interfere with or otherwise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as antisense agents in human clinical trials for various disease states, including use as antiviral agents.

Transcription factors interact with double-stranded DNA during regulation of transcription. Oligonucleotides can serve as competitive inhibitors of transcription factors to modulate their action. Several recent reports describe such interactions (see Bielinska, A., et. al., *Science*, 1990, 250, 997–1000; and Wu, H., et. al., *Gene*, 1990, 89, 203–209).

In addition to such use as both indirect and direct regulators of proteins, oligonucleotides and their analogs also have found use in diagnostic tests. Such diagnostic tests can be performed using biological fluids, tissues, intact cells or isolated cellular components. As with gene expression inhibition, diagnostic applications utilize the ability of oligonucleotides and their analogs to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual*, supra. See also "DNA-protein interactions and The Polymerase Chain Reaction" in Vol. 2 of *Current Protocols In Molecular Biology*, supra.

Oligonucleotides and their analogs can be synthesized to have customized properties that can be tailored for desired uses. Thus a number of chemical modifications have been introduced into oligomeric compounds to increase their usefulness in diagnostics, as research reagents and as therapeutic entities. Such modifications include those designed to increase binding to a target strand (i.e. increase their melting temperatures, Tm), to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

The chemical literature discloses numerous processes for coupling nucleosides through phosphorous-containing covalent linkages to produce oligonucleotides of defined sequence. One of the most popular processes is the phosphoramidite technique (see, e.g., Advances in the Synthesis of Oligonucleotides by the Phosphoramidite Approach, Beaucage, S. L.; Iyer, R. P., *Tetrahedron*, 1992, 48, 2223–2311 and references cited therein), wherein a nucleoside or oligonucleotide having a free hydroxyl group is reacted with a protected cyanoethyl phosphoramidite monomer in the presence of a weak acid to form a phosphite-linked structure. Oxidation of the phosphite linkage followed by hydrolysis of the cyanoethyl group yields the desired phosphodiester or phosphorothioate linkage.

The phosphoramidite technique, however, has significant disadvantages. For example, cyanoethyl phosphoramidite monomers are quite expensive. Although considerable quantities of monomer go unreacted in a typical phosphoramidite coupling, unreacted monomer can be recovered, if at all, only with great difficulty.

Another disadvantage of using a β-eliminating cyanoethoxy group is formation of acrylonitrile upon removal of the phosphorus protecting group. Acrylonitrile is a highly toxic agent as well as a suspected carcinogen (See 1994-1995 Aldrich Chemical Company Catalog, at page 32). Acrylonitrile is also suspected of forming cyclic structures with thymidine resulting in oligomeric compounds having decreased hybridization ability. These modified oligomeric compounds are undesirable because they are difficult to separate from the desired oligomeric compound.

Consequently, there remains a need in the art for synthetic methods that will overcome these problems.

Several processes are known for the solid phase synthesis of oligonucleotide compounds. These are generally disclosed in the following U.S. Pat. No. 4,458,066; issued Jul. 3, 1984; U.S. Pat. No. 4,500,707, issued Feb. 19, 1985; and U.S. Pat. No. 5,132,418, issued Jul. 21, 1992. Additionally, a process for the preparation of oligonucleotides using phosphoramidite intermediates is disclosed in U.S. Pat. No. 4,973,679, issued Nov. 27, 1990.

A process for the preparation of phosphoramidites is disclosed in U.S. Pat. No. 4,415,732, issued Nov. 15, 1983.

Phosphoramidite nucleoside compounds are disclosed in U.S. Pat. No. 4,668,777, issued May 26, 1987.

A process for the preparation of oligonucleotides using a β-eliminating phosphorus protecting group is disclosed in U.S. Pat. No. Re. 34,069, issued Sep. 15, 1992.

A process for the preparation of oligonucleotides using a β-eliminating or allylic phosphorus protecting group is disclosed in U.S. Pat. No. 5,026,838, issued Jun. 25, 1991.

SUMMARY OF THE INVENTION

It is an object of the present invention to provide methods for the preparation of oligomeric compounds having phosphite, phosphodiester, phosphorothioate, or phosphorodithioate containing covalent linkages. It is a further object of the present invention to provide synthetic intermediates useful in such processes. Other objects will be apparent to those skilled in the art.

These objects are satisfied by the present invention, which provides methods for the preparation of oligomeric compounds having phosphite, phosphodiester, phosphorothioate, or phosphorodithioate containing covalent linkages.

In one aspect of the present invention, methods are provided for the preparation of oligomeric compounds comprising a moiety having the Formula IX:

IX wherein:

Z is CN, —Si($R_9$)$_3$, halogen, $NO_2$, alkaryl, sulfoxyl, sulfonyl, thio, substituted sulfoxyl, substituted sulfonyl, or substituted thio, wherein the substituents are selected from the group consisting of alkyl, aryl, or alkaryl;

each $R_9$ is, independently, alkyl having 1 to about 10 carbon atoms, or aryl having 6 to about 10 carbon atoms;

$X_1$ is O or S;

comprising the steps of:

(a) providing a compound having the Formula II:

II wherein:

each $R_1$, is, independently, H, —OH, —F, or —O—$X_3$—D;

$X_3$ is alkyl having from 1 to 10 carbons;

D is H, amino, protected amino, alkyl substituted amino, imidazole, or (—O—$X_3$)$_p$, where p is 1 to about 10;

each $X_2$ is O or S;

$R_3$ and $R_{3a}$ are each hydrogen, a hydroxyl protecting group, or a linker connected to a solid support;

each B, independently, is a naturally occurring or non-naturally occurring nucleobase or a protected naturally occurring or non-naturally occurring nucleobase;

n is 0 to about 50;

each Q is —$X_1$H or —$X_1$—$CH_2$—CH=CH—$CH_2$—Z;

$R_5$ is —N($R_6$)$_2$, or a heterocycloalkyl or heterocycloalkenyl ring containing from 4 to 7 atoms, and having up to 3 heteroatoms selected from the group consisting of nitrogen, sulfur, and oxygen;

$R_6$ is straight or branched chain alkyl having from 1 to 10 carbons;

(b) reacting the compound of Formula II with a compound having the Formula III:

III wherein $R_{3a}$ is hydrogen; and $R_2$ is a hydroxyl protecting group, or a linker connected to a solid support, provided that $R_2$ and $R_3$ are not both simultaneously a linker connected to a solid support; to form the oligomeric compound.

Some preferred embodiments of the methods of the invention further comprise the step of oxidizing the oligomeric compound. In some preferred embodiments, the methods of the invention further comprise transforming the oxidized oligomeric compound to form a further compound having the Formula III, where n is increased by 1.

Preferably, the methods of the invention comprise a capping step, either prior to or after the oxidation step.

Other preferred embodiments of the invention further comprise the step of cleaving the oligomeric compound to produce a compound having the Formula I:

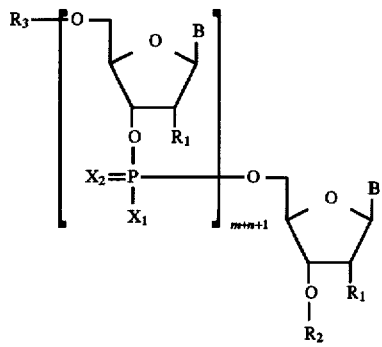

In some preferred embodiments of the invention, Z is CN. In other preferred embodiments of the invention, each $R_6$ is isopropyl.

In preferred embodiments, $X_1$ and $X_2$ can each independently be O or S.

In some preferred embodiments the compound of Formula II is obtained by reaction of a compound having the Formula V:

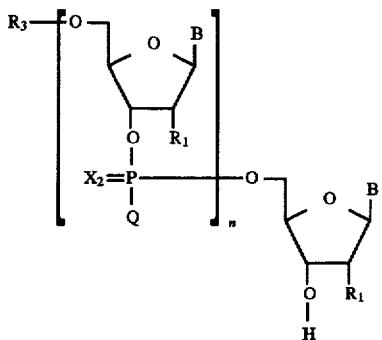

with a compound having the Formula VI:

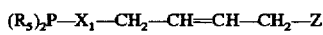

$(R_5)_2P-X_1-CH_2-CH=CH-CH_2-Z$     VI in the presence of an acid. Preferably, $R_5$ is N,N-diisopropylamino.

Also provided in accordance with the invention are novel compounds having the Formula VII:

$A-X_1-CH_2-CH=CH-CH_2-Z$     VII wherein:

$X_1$ is O or S;

A is $(R_7)(R_8)P-$;

$R_8$ is $R_5$, or has the Formula X:

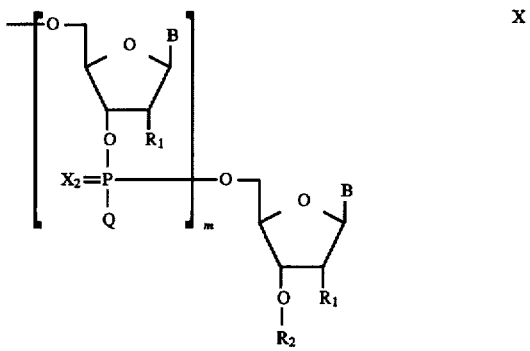

wherein:

each $R_1$, is, independently, H, —OH, —F, —O—$X_3$—D;

$X_3$ is alkyl having from 1 to 10 carbons;

D is H, amino, protected amino, alkyl substituted amino, imidazole, or (—O—$X_3$)$_p$, where p is 1 to about 10;

each $X_2$ is O or S;

$R_5$ is —N($R_6$)$_2$, or a heterocycloalkyl or heterocycloalkenyl ring containing from 4 to 7 atoms, and having up to 3 heteroatoms selected from the group consisting of nitrogen, sulfur, and oxygen;

each Q is —$X_1$H or —$X_1$—CH$_2$—CH=CH—CH$_2$—Z;

m is 0 to about 50;

each B, independently, is a naturally occurring or non-naturally occurring nucleobase or a protected naturally occurring or non-naturally occurring nucleobase; and $R_7$ is $R_5$, or has the Formula VIII:

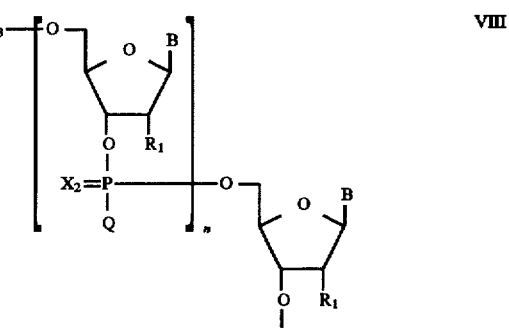

wherein:

$R_3$ is hydrogen, a hydroxyl protecting group, or a linker connected to a solid support; and n is 0 to about 50; with the proviso that the sum of m and n do not exceed 50; and Z is CN, —Si($R_9$)$_3$, halogen, NO$_2$, alkaryl, sulfoxyl, sulfonyl, thio, substituted sulfoxyl, substituted sulfonyl, or substituted thio, wherein the substituents are selected from the group consisting of alkyl, aryl, or alkaryl;

each $R_9$ is, independently, alkyl having 1 to about 10 carbon atoms, or aryl having 6 to about 10 carbon atoms;

In some preferred embodiments of the compounds of the invention Z is CN. In other preferred embodiments Z is Si($R_9$)$_3$. In further preferred embodiments A is H or —P($R_5$)$_2$.

In some preferred embodiments $R_5$ is —N(CH(CH$_3$)$_2$)$_2$, and other preferred embodiments $R_7$ has the Formula VII.

Preferably, n is 1 to 30, with 1 to about 20 being more preferred. In some preferred embodiments n is 0.

In more preferred embodiments, Z is CN, $X_1$ is O, and A is H; or Z is CN; $X_1$ is S; and A is H. In other preferred embodiments Z is CN, $X_1$ is O, and each $R_6$ is isopropyl. In further preferred embodiments Z is CN, $X_1$ is S, and each $R_6$ is isopropyl.

In particularly preferred embodiments, the compounds of the invention have the Formula IV:

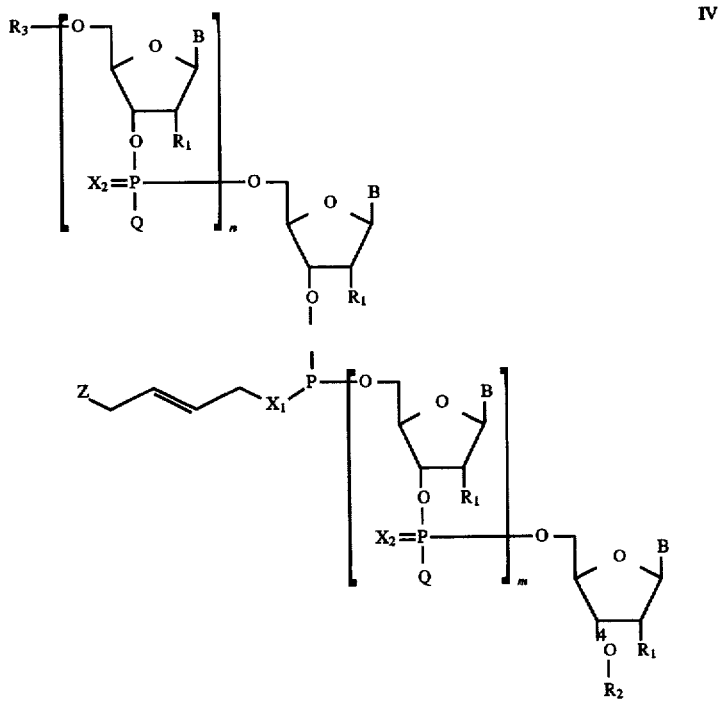

IV wherein $R_2$ is preferably a linker connected to a solid support, or hydrogen.

In preferred embodiments m and n are each 0; or Z is CN, and $X_1$ is O.

The present invention also provides products produced by the methods of the invention.

DESCRIPTION OF PREFERRED EMBODIMENTS

The present invention provides methods for the preparation of oligomeric compounds having phosphite, phosphodiester, phosphorothioate, or phosphorodithioate linkages, and to intermediates useful in their preparation.

In some preferred embodiments of the invention, methods are provided for the preparation of an oligomeric compound comprising a moiety having the Formula IX:

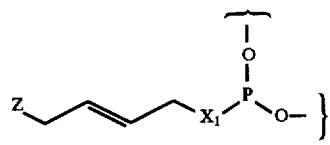

IX wherein:

Z is CN, —Si($R_9$)$_3$, halogen, $NO_2$, alkaryl, sulfoxyl, sulfonyl, thio, substituted sulfoxyl, substituted sulfonyl, or substituted thio, wherein the substituents are selected from the group consisting of alkyl, aryl, or alkaryl;

each $R_9$ is, independently, alkyl having 1 to about 10 carbon atoms, or aryl having 6 to about 10 carbon atoms;

$X_1$ is O or S; comprising the steps of:

(a) providing a compound having the Formula II:

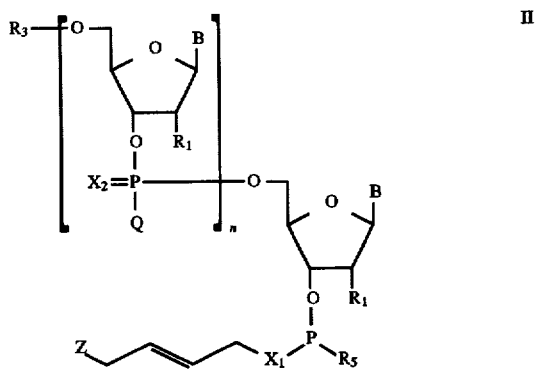

II wherein:

each $R_1$, is, independently, H, —OH, —F, or —O—$X_3$—D;

$X_3$ is alkyl having from 1 to 10 carbons;

D is H, amino, protected amino, alkyl substituted amino, imidazole, or (—O—$X_3$)$_p$, where p is 1 to about 10;

each $X_2$ is O or S;

$R_3$ and $R_{3a}$ are each hydrogen, a hydroxyl protecting group, or a linker connected to a solid support;

each B, independently, is a naturally occurring or non-naturally occurring nucleobase or a protected naturally occurring or non-naturally occurring nucleobase;

n is 0 to about 50;

each Q is —$X_1H$ or —$X_1$—$CH_2$—CH=CH—$CH_2$—Z;

$R_5$ is —$N(R_6)_2$, or a heterocycloalkyl or heterocycloalkenyl ring containing from 4 to 7 atoms, and having up to 3 heteroatoms selected from the group consisting of nitrogen, sulfur, and oxygen;

$R_6$ is straight or branched chain alkyl having from 1 to 10 carbons;

(b) reacting the compound of Formula II with a compound having the Formula III:

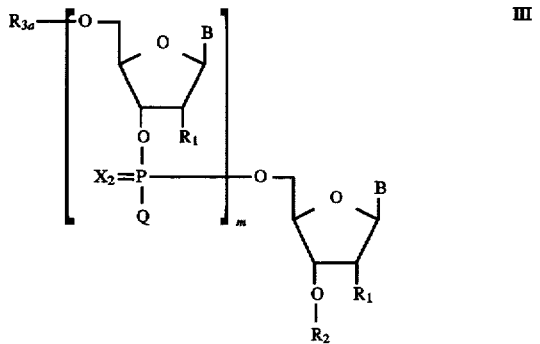

III wherein $R_{3a}$ is hydrogen;and $R_2$ is a hydroxyl protecting group, or a linker connected to a solid support, provided that $R_2$ and $R_3$ are not both simultaneously a linker connected to a solid support;

to form the oligomeric compound.

The methods of the present invention are useful for the preparation of oligomeric compounds containing monomeric subunits that are joined by a variety of linkages, including phosphite, phosphodiester, phosphorothioate, and/or phosphorodithioate linkages. As used herein, the term "oligomeric compound" is used to refer to compounds containing a plurality of monomer subunits that are joined by phosphite, phosphodiester, phosphorothioate, and/or phosphorodithioate linkages. Oligomeric compounds include oligonucleotides, their analogs, and synthetic oligonucleotides. Monomer or higher order synthons having Formulas II or III above include both native (i.e., naturally occurring) and synthetic (e.g., modified native of totally synthetic) nucleosides.

In preferred embodiments, compounds of Formula II and Formula III are reacted to produce compounds of Formula IV. Methods for coupling compounds of Formula II and Formula III of the invention include both solution phase and solid phase chemistries. Representative solution phase techniques are described in U.S. Pat. No. 5,210,264, which is assigned to the assignee of the present invention. In preferred embodiments, the methods of the present invention are employed for use in iterative solid phase oligonucleotide synthetic regimes. Representative solid phase techniques are those typically employed for DNA and RNA synthesis utilizing standard phosphoramidite chemistry, (see, e.g., Protocols For Oligonucleotides And Analogs, Agrawal, S., ed., Humana Press, Totowa, N.J., 1993). A preferred synthetic solid phase synthesis utilizes phosphoramidites as activated phosphate compounds. In this technique, a phosphoramidite monomer is reacted with a free hydroxyl on the growing oligomer chain to produce an intermediate phosphite compound, which is subsequently oxidized to the $P^V$ state using standard methods. This technique is commonly used for the synthesis of several types of linkages including phosphodiester, phosphorothioate, and phosphorodithioate linkages.

Typically, the first step in such a process is attachment of a first monomer or higher order subunit containing a protected 5'-hydroxyl to a solid support, usually through a linker, using standard methods and procedures known in the art. The support-bound monomer or higher order first synthon is then treated to remove the 5'-protecting group, to form a compound of Formula III wherein $R_2$ is a linker connected to a solid support. Typically, this is accomplished by treatment with acid. The solid support bound monomer is then reacted with a compound of Formula II to form a compound of Formula IV, which has a phosphite or thiophosphite linkage of Formula IX. In preferred embodiments, synthons of Formula II and Formula III are reacted under anhydrous conditions in the presence of an activating agent such as, for example, 1H-tetrazole, 5-(4-nitrophenyl)-1H-tetrazole, or diisopropylamino tetrazolide.

In preferred embodiments, phosphite or thiophosphite compounds containing a linkage of Formula IX are oxidized as shown below to produce compounds having a linkage of Formula XI, where $X_1$ and $X_2$ can each be O or S:

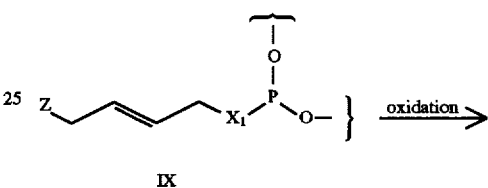

IX

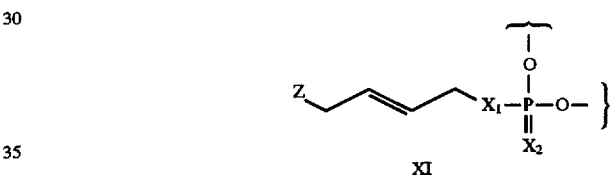

XI

Choice of oxidizing agent will determine whether the linkage of Formula IX is oxidized to a phosphotriester, thiophosphotriester, or a dithiophosphotriester linkage.

It is generally preferable to perform a capping step, either prior to or after oxidation of the phosphite triester, thiophosphite triester, or dithiophosphite triester. Such a capping step is generally known to provide benefits in the prevention of shortened oligomer chains, by blocking chains that have not reacted in the coupling cycle. One representative reagent used for capping is acetic anhydride. Other suitable capping reagents and methodologies can be found in U.S. Pat. No. 4,816,571, issued Mar. 28, 1989.

Treatment with an acid removes the 5'-hydroxyl protecting group, and thus transforms the solid support bound oligomer into a further compound of Formula III wherein $R_{3a}$ is hydrogen, which can then participate in the next synthetic iteration; i.e., which can then be reacted with a further compound of Formula II. This process is repeated until an oligomer of desired length is produced.

The completed oligomer is then cleaved from the solid support. The cleavage step, which can precede or follow deprotection of protected functional groups, will yield a compound having the Formula I wherein $R_2$ is hydrogen. During cleavage, the linkages between monomeric subunits are converted from phosphotriester, thiophosphotriester, or dithiophosphotriester linkages to phosphodiester, phosphorothioate, or phosphorodithioate linkages. This conversion is effected through the loss of an oxygen or sulfur protecting group of Formula Z—$CH_2$—CH=CH—$CH_2$—. Depending upon the species Z, it is believed that the loss of an oxygen or sulfur protecting group occurs via either a δ-elimination mechanism, or a δ-fragmentation mechanism.

While not wishing to be bound by a particular theory, it is believed that the loss of the oxygen or sulfur protecting group where Z is a non-silyl electron withdrawing group occurs via a δ-elimination mechanism, illustrated in Scheme I below:

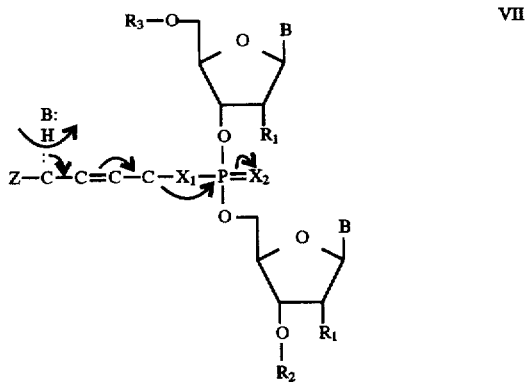

VII

In this mechanism, a base first abstracts an acidic proton from the carbon atom adjacent to electron withdrawing group Z. The resonant movement of electrons as depicted in Scheme I above is believed to cause the loss of the oxygen or sulfur protecting group via a δ-elimination, thereby forming a phosphodiester, phosphorothioate, or phosphorodithioate linkage. The other product of the deprotection is a 1-substituted-1,3-butadiene, having electron withdrawing substituent Z at the 1-position.

Substituent Z can be an electron withdrawing group selected such that it facilitates the abstraction of a proton from the adjacent carbon atom by resonance, inductive, or other electron withdrawing mechanisms. Accordingly, Z can be any of a variety of electron withdrawing substituents, provided that it does not otherwise interfere with the methods of the invention. Preferred non-silyl electron withdrawing Z groups include CN, halogens, $NO_2$, alkaryl groups, sulfoxyl groups, sulfonyl groups, thio groups, substituted sulfoxyl groups, substituted sulfonyl groups, or substituted thio groups, wherein the substituents are selected from the group consisting of alkyl, aryl, or alkaryl. In more preferred embodiments Z is cyano.

Z can also be a trisubstituted silyl moiety, wherein the substituents are alkyl, aryl or both. While not wishing to be bound by a particular theory, it is believed that the loss of the oxygen or sulfur protecting group, where Z is such a trisubstituted silyl moiety, occurs via a δ-fragmentation mechanism, illustrated in Scheme II below:

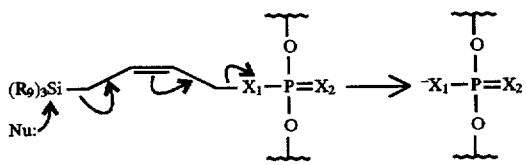

In this scheme, a nucleophile attacks the silyl silicon atom, and the resonant movement of electrons as depicted in Scheme II above is believed to cause the loss of the oxygen or sulfur protecting group via a δ-fragmentation mechanism, thereby forming a phosphodiester, phosphorothioate, or phosphorodithioate linkage. The other products of the deprotection are 1,3-butadiene, and $Nu-Si(R_3)_3$.

A wide variety of bases can be used to initiate the δ-elimination of the oxygen or sulfur protecting group. These include aqueous ammonium hydroxide, aqueous methylamine, or DBU (1,8-diazabicyclo[5.4.0]undec-7-ene).

A wide variety of nucleophiles can be used to initiate the δ-fragmentation of the oxygen or sulfur protecting group. These include ammonium hydroxide, fluoride ion, alkyl amines, aqueous bases, and alkyl amines in combination with ammonium hydroxide. The resulting products include phosphate, phosphorothioate, and phosphorodithioate containing compounds.

Contact with fluoride ion preferably is effected in a solvent such as tetrahydrofuran, acetonitrile, dimethoxyethane, or water. Fluoride ion preferably is provided in the form of one or more salts selected from tetraalkylammonium fluorides (e.g., tetrabutylammonium fluoride (TBAF)), potassium fluoride, or cesium fluoride.

Preferably, conditions for removal of the oxygen or sulfur protecting group via δ-elimination or δ-fragmentation also effect cleavage of the oligomeric compound from the solid support.

The methods of the present invention are applicable to the synthesis of a wide variety of oligomeric compounds which contain phosphite, phosphodiester, phosphorothioate, or phosphorodithioate linkages. As used herein, the term "oligomeric compound" denotes a polymeric compound containing two or more monomeric subunits joined by such phosphite, phosphodiester, phosphorothioate, or phosphorodithioate linkages.

In preferred embodiments, the methods of the invention are used for the preparation of oligonucleotides and their analogs. As used herein, the term "oligonucleotide analog" means compounds that can contain both naturally occurring (i.e. "natural") and non-naturally occurring ("synthetic") moieties, for example, nucleosidic subunits containing modified sugar and/or nucleobase portions. Such oligonucleotide analogs are typically structurally distinguishable from, yet functionally interchangeable with, naturally occurring or synthetic wild type oligonucleotides. Thus, oligonucleotide analogs include all such structures which function effectively to mimic the structure and/or function of a desired RNA or DNA strand, for example, by hybridizing to a target. The term synthetic nucleoside, for the purpose of the present invention, refers to a modified nucleoside. Representative modifications include modification of a heterocyclic base portion of a nucleoside to give a non-naturally occurring nucleobase, a sugar portion of a nucleoside, or both simultaneously.

Representative nucleobases include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in *Antisense Research and Application*, Ed. S. T. Crooke and B. Lebleu, CRC Press, 1993, in Englisch et al., *Angewandte Chemie*, International Edition, 1991, 30, 613–722 (see especially pages 622 and 623, and in the Concise *Encyclopedia of Polymer Science and Engineering*, J. I. Kroschwitz Ed., John Wiley & Sons, 1990, pages 858–859, Cook, P. D., *Anti-Cancer Drug Design*, 1991, 6, 585–607. The term 'nucleosidic base' is further intended to include heterocyclic compounds that can serve as like nucleosidic bases including certain 'universal bases' that are not nucleosidic bases in the most classical sense but serve as nucleosidic bases. Especially mentioned as a universal base is 3-nitropyrrole.

Representative 2' sugar modifications (position $R_1$) amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249. Further sugar modifications are disclosed in Cook, P. D., supra. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions.

Sugars having O-substitutions on the ribosyl ring are also amenable to the present invention. Representative substitutions for ring O include S, $CH_2$, CHF, and $CF_2$, see, e.g., Secrist, et al., *Abstract* 21, *Program & Abstracts, Tenth International Roundtable, Nucleosides, Nucleotides and their Biological Applications*, Park City, Utah, Sep. 16–20, 1992.

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41–50.

As used herein, the term "aralkyl" denotes alkyl groups which bear aryl groups, for example, benzyl groups. The term "alkaryl" denotes aryl groups which bear alkyl groups, for example, methylphenyl groups. "Aryl" groups are aromatic cyclic compounds including but not limited to phenyl, naphthyl, anthracyl, phenanthryl, pyrenyl, and xylyl.

As used herein, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

In some preferred embodiments of the invention $R_2$, $R_3$ or $R_{3a}$ can be a linker connected to a solid support. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. No. 4,725,677 and U.S. Pat. No. Re. 34,069. Linkers are known in the art as short molecules which serve to connect a solid support to functional groups (e.g., hydroxyl groups) of initial synthon molecules in solid phase synthetic techniques. Suitable linkers are disclosed in, for example, *Oligonucleotides And Analogues A Practical Approach*, Ekstein, F. Ed., IRL Press, N.Y., 1991, Chapter 1, pages 1–23.

Solid supports according to the invention include those generally known in the art to be suitable for use in solid phase methodologies, including, for example, controlled pore glass (CPG), oxalyl-controlled pore glass (see, e.g., Alul, et al., *Nucleic Acids Research* 1991, 19, 1527), Tenta-Gel Support—an aminopolyethyleneglycol derivatized support (see, e.g., Wright, et al., *Tetrahedron Letters* 1993, 34, 3373) and Poros—a copolymer of polystyrene/ divinylbenzene.

In some preferred embodiments of the invention $R_2$, $R_3$ or $R_{3a}$ can be a hydroxyl protecting group. A wide variety of hydroxyl protecting groups can be employed in the methods of the invention. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage, et al., *Tetrahedron* 1992, 48, 2223–2311, and also in Greene and Wuts, *Protective Groups in Organic Synthesis*, Chapter 2, 2d ed, John Wiley & Sons, New York, 1991. Preferred protecting groups used for $R_2$, $R_3$ and $R_{3a}$ include dimethoxytrityl (DMT), monomethoxytrityl, 9-phenylxanthen-9-yl (Pixyl) and 9-(p-methoxyphenyl)xanthen-9-yl (Mox). The $R_2$ or $R_3$ group can be removed from oligomeric compounds of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide. See for example, Greene and Wuts, supra.

In some preferred embodiments of the invention amino groups are appended to alkyl or other groups, such as, for example, 2'-alkoxy groups (e.g., where $R_1$ is alkoxy). Such amino groups are also commonly present in naturally occurring and non-naturally occurring nucleobases. It is generally preferred that these amino groups be in protected form during the synthesis of oligomeric compounds of the invention. Representative amino protecting groups suitable for these purposes are discussed in Greene and Wuts, Protective Groups in *Organic Synthesis*, Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

Sulfurizing agents used during oxidation to form phosphorothioate and phosphorodithioate linkages include Beaucage reagent (see e.g. Iyer, R. P., et.al., *J. Chem. Soc.,* 1990, 112, 1253–1254, and Iyer, R. P., et.al., *J. Org. Chem.,* 1990, 55, 4693–4699); tetraethylthiuram disulfide (see e.g., Vu, H., Hirschbein, B. L., *Tetrahedron Lett.*, 1991, 32, 3005–3008); dibenzoyl tetrasulfide (see e.g., Rao, M. V., et.al., *Tetrahedron Lett.*, 1992, 33, 4839–4842); di(phenylacetyl)disulfide (see e.g., Kamer, P. C. J., *Tetrahedron Lett.*, 1989, 30, 6757–6760); sulfur, sulfur in combination with ligands like triaryl, trialkyl, triaralkyl, or trialkaryl phosphines.

Useful oxidizing agents used to form the phosphodiester or phosphorothioate linkages include iodine/ tetrahydrofuran/water/pyridine or hydrogen peroxide/water or tert-butyl hydroperoxide or any peracid like m-chloroperbenzoic acid. In the case of sulfurization the reaction is performed under anhydrous conditions with the exclusion of air, in particular oxygen whereas in the case of oxidation the reaction can be performed under aqueous conditions.

Oligonucleotides or oligonucleotide analogs according to the present invention hybridizable to a specific target preferably comprise from about 5 to about 50 monomer subunits. It is more preferred that such compounds comprise from about 10 to about 30 monomer subunits, with 15 to 25 monomer subunits being particularly preferred. When used as "building blocks" in assembling larger oligomeric compounds (i.e., as synthons of Formula II), smaller oligomeric compounds are preferred. Libraries of dimeric, trimeric, or higher order compounds of general Formula II can be prepared for use as synthons in the methods of the invention. The use of small sequences synthesized via solution phase chemistries in automated synthesis of larger oligonucleotides enhances the coupling efficiency and the purity of the final oligonucleotides. See for example: Miura, K., et al., *Chem. Pharm. Bull.*, 1987, 35, 833–836; Kumar, G., and Poonian, M. S., *J. Org. Chem.*, 1984, 49, 4905–4912; Bannwarth, W., *Helvetica Chimica Acta*, 1985, 68, 1907–1913; Wolter, A., et al., *nucleosides and nucleotides*, 1986, 5, 65–77.

In one aspect of the invention, the compounds of the invention are used to modulate RNA or DNA, which code for a protein whose formation or activity it is desired to modulate. The targeting portion of the composition to be employed is, thus, selected to be complementary to the preselected portion of DNA or RNA, that is to be hybridizable to that portion.

In preferred embodiments of the methods of the invention, the compound of Formula II is prepared by reaction of a protected nucleoside having Formula V:

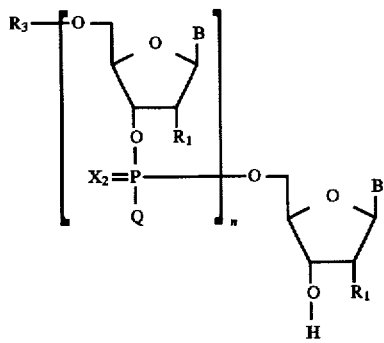

and a phosphine compound of Formula VI:

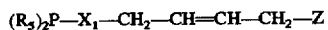

in the presence of an acid. Suitable acids include those known in the art to be useful for coupling of phosphoramidites, including, for example, diisopropylammonium tetrazolide.

Compounds of Formula VI are preferably prepared by reacting an alcohol having the formula $HOCH_2CH=CHCH_2Z$ with phosphorus trichloride, and reacting the resultant product, $Cl_2PX_1CH_2CH=CHCH_2Z$, with at least two equivalents of an amine having the formula $[(R_6)_2N]_2NH$. Each of the $R_6$ groups can be the same or different, and are preferably alkyl having 1 to about 10 carbon atoms, more preferably 1 to 6 carbon atoms, with 3 carbon atoms, and particularly isopropyl groups, being especially preferred.

$X_1$ and $X_2$ can each independently be O or S. Thus, compounds having chiral phosphorus linkages are contemplated by the present invention. See Stec, W. J., and Lesnikowski, Z. J., in *Methods in Molecular Biology Vol. 20: Protocols for Oligonucleotides and Analogs*, S. Agrawal, Ed., Humana Press, Totowa, N.J. (1993), at Chapter 14. See also Stec, W. J. et al., *Nucleic Acids Research*, Vol. 19, No. 21, 5883–5888 (1991); and European Patent Application EP 0 506 242 A1.

Also provided in preferred embodiments of the invention are compounds having the general Formula VII:

wherein $X_1$, A, and Z are as defined above.

The oligomeric compounds of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLE 1

1-Chloro-2-butene-4-ol

2-Butene-1,4-diol (600 g, 6.81 mol) was added to a 5-liter three-necked round bottomed flask equipped with a condenser, a pressure equalizing addition funnel and a mechanical stirrer. To this was added anhydrous ether (1400 mL) and pyridine (604.9 mL, 7.49 mol). The reaction flask was cooled to 0° C. and thionyl chloride (545.6 mL, 7.49 mol) was added dropwise over a period of 2.5 hours. After the addition was complete, the reaction mixture was allowed to warm to room temperature and stirred overnight. The reaction mixture was then poured into 500 mL of ice water and extracted with ether (2×400 mL). The combined ether extracts were washed with saturated sodium bicarbonate followed by brine and dried ($Na_2SO_4$). Concentration of the dried extracts gave the title compound which was used in the next step without further purification.

EXAMPLE 2

4-Cyano-2-butene-1-ol

1-Chloro-2-butene-4-ol (230 g, 2.14 mol) was dissolved in anhydrous acetonitrile (1250 mL) and added to a 3 L round bottomed flask under an atmosphere of argon. Potassium cyanide (825 g, 12.5 mol) was added all at once and the reaction was stirred at room temperature for 3 hours. NaI (16 g, 0.054 mol) was added and the reaction mixture was stirred overnight at room temperature. The reaction mixture was filtered and the solid washed with ethyl acetate (800 mL). Concentration of the filtrate in vacuo afforded an oil which was triturated with ether (750 mL). This mixture was filtered and the clear filtrate concentrated. The crude product was distilled using a short path to give the title compound, bp 89°–91° C. at 0.2 mm Hg. IR (neat) cm$^{-1}$: 3400, 2900, 2250, 1650.

EXAMPLE 3

4-Cyano-2-butenyl-N,N,N',N'-tetraisopropylphosphorodiamidite

A 500 mL three-necked flask equipped with a magnetic stirrer, a glass stopper and an inlet for argon is assembled under an atmosphere of argon. All the glassware is dried in an oven at 120° C. for 1 hour. Anhydrous ether (150 mL) and phosphorous trichloride (67.5 mmol) is added to the flask. 4-Cyanobutene-1-ol (50 mmol) in ether (50 mL) is added to the reaction flask slowly with stirring at 0° C. (ice bath) using a pressure-equalized addition funnel. After the addition is complete, the ice bath is removed and the reaction is stirred for three hours at room temperature. The reaction mixture is then transferred to a 500 mL flask and concentrated under reduced pressure.

To the product in anhydrous ether (200 mL) is added diisopropylamine (57.7 mL) at 0° C. under argon. After the addition is complete, stirring is continued at room temperature for 16 hours. The reaction mixture is filtered and concentrated to afford the title compound.

EXAMPLE 4

Preparation of protected phosphoramidite monomers
A. 5'-O-DMT-thymidine-3'-O-(4-cyano-2-butenyl N,N-diisopropylphosphoramidite)

A 250 mL two-necked flask equipped with a magnetic stirrer, a gas inlet for argon, and a septum is assembled under an atmosphere of argon. All the glassware is dried at 120° C. for 1 hour. 5'-O-DMT-thymidine (7 mmol) and 5-(4-nitrophenyl)1H-tetrazole (5.6 mmol) and anhydrous acetonitrile (50 mL) is added to the flask. To this stirred mixture at room temperature is added a solution of 4-cyano-2-butenyl-N,N,N',N'-tetraisopropylphosphorodiamidite (10.5 mmol) in acetonitrile (50 mL). After stirring for two hours, the reaction mixture is filtered and the filtrate diluted with ethyl acetate (100 mL), washed once with cold saturated sodium bicarbonate solution, brine and dried (MgSO$_4$). The dried solution is concentrated under reduced pressure and purified by silica gel flash column chromatography to give the title compound.
B. N2-Isobutyryl-5'-O-DMT-2'-deoxyguanosine-3'-O-(4-cyano-2-butenyl N,N-diisopropylphosphoramidite)

A 250 mL two-necked flask equipped with a magnetic stirrer, a gas inlet for argon, and a septum is assembled under an argon atmosphere. All the glassware is dried at 120° C. for 1 hour. The flask is charged with N2-isobutyryl-5'-O-DMT-2'-deoxyguanosine (5 mmol) and diisopropyl ammonium tetrazolide (4 mmol). Anhydrous acetonitrile (50 mL) is added. To this stirred mixture at room temperature is added a solution of 4-cyano-2-butenyl-N,N,N',N'-tetraisopropylphosphorodiamidite (7.5 mmol) in acetonitrile (50 mL). After stirring for two hours, the reaction mixture is filtered and the filtrate diluted with ethyl acetate (100 mL), washed once with cold saturated sodium bicarbonate solution, brine and dried (MgSO$_4$). The dried solution is concentrated under reduced pressure to afford the product which is purified by silica gel flash column chromatography.

C. N6-Benzoyl-5'-O-DMT-2'-deoxyadenosine-3'-O-(4-cyano-2-butenyl N,N-diisopropylphosphoramidite)

A 250 mL two-necked flask equipped with a magnetic stirrer, a gas inlet for argon, and a septum is assembled under an atmosphere of argon. All the glassware is dried at 120° C. for 1 hour. The flask is charged with N6-benzoyl-5'-O-DMT-2'-deoxyadenosine (5 mmol) and diisopropylammonium tetrazolide (4 mmol). Anhydrous acetonitrile (50 mL) is added. To this stirred mixture at room temperature is added a solution of 4-cyano-2-butenyl-N,N,N',N'-tetraisopropylphosphorodiamidite (6 mmol) in acetonitrile (50 mL). After stirring for two hours, the reaction mixture is filtered and concentrated to a residue which is purified by silica gel flash column chromatography to give the title compound.
D. N4-Benzoyl-5'-O-DMT-2'-deoxycytidine-3'-O-(4-cyano-2-butenyl N,N-diisopropylphosphoramidite)

A 250 mL two-necked flask equipped with a magnetic stirrer, a gas inlet for argon, and a septum is assembled under an atmosphere of argon. All the glassware is dried at 120° C. for 1 hour. The flask is charged with N4-benzoyl-5'-O-DMT-2'-deoxycytidine (5 mmol) and diisopropylammonium tetrazolide (4 mmol). Anhydrous acetonitrile (50 mL) is added. To this stirred mixture at room temperature is added a solution of 4-cyano-2-butenyl-N,N,N',N'-tetraisopropylphosphorodiamidite (7.5 mmol) in acetonitrile (50 mL). After stirring for two hours, the reaction mixture is filtered and the filtrate diluted with ethyl acetate (100 mL), washed once with cold saturated sodium bicarbonate solution, brine and dried (MgSO$_4$). The dried solution is concentrated under reduced pressure to afford the product which is purified by silica gel flash column chromatography.

EXAMPLE 5

Coupling Procedures
A. Synthesis of T-T phosphorothioate dimer 100 milligram (4 mmole) of 5'-O-DMT-thymidine bonded to CPG (controlled pore glass) through an ester linkage is transferred to a glass reactor, and a dichloromethane solution of 2% dichloroacetic acid (volume/volume) is added to deprotect the 5'-hydroxyl group. The product is washed with dichloromethane and then with acetonitrile. Then, a 0.2M solution of 5'-O-DMT-thymidine-3'-O-(4-cyano-2-butenyl N,N-diisopropylphosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

The carrier containing the compound is treated with 30% aqueous ammonium hydroxide solution for 24 hours at 65° C. The aqueous solution is filtered, concentrated under reduced pressure to give the phosphorothioate dimer of T-T.
B. Synthesis of C-T phosphorothioate dimer 5'-O-DMT-thymidine (100 mg, 4 mmole) bonded to CPG (controlled pore glass) through an ester linkage is transferred to a glass reactor, and a CH$_2$CHl$_2$ solution of 2% dichloroacetic acid (v/v) is added to deprotect the 5'-hydroxyl group. The product is washed with acetonitrile. Then, a 0.2M solution of N4-Benzoyl-5'-O-DMT-2'-deoxycytidine-3'-O-(4-cyano-2-butenyl N,N-diisopropylphosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl groups. The product is washed with acetonitrile.

The carrier containing the compound is treated with 30% aqueous ammonium hydroxide solution for 24 hours at 65° C. The aqueous solution is filtered, concentrated under reduced pressure to give the phosphorothioate dimer of dC-T.

C. Synthesis of T-T phosphodiester dimer

5'-O-DMT-thymidine (100 mg, 4 mmole) bonded to CPG through an ester linkage is transferred to a glass reactor, and a $CH_2CHl_2$ solution of 2% dichloroacetic acid (v/v) is added to deprotect the 5'-hydroxyl group. The product is washed with $CH_2CHl_2$ and then with acetonitrile. Then, a 0.2M solution of 5'-O-DMT-thymidine-3'-O-(4-cyano-2-butenyl N,N-diisopropylphosphoramidite) in acetonitrile and a 0.4M solution of 1H-tetrazole in acetonitrile is added, and reacted at room temperature for 5 minutes. The product is washed with acetonitrile, and then 0.1M iodine in water/pyridine/THF (2:20:80, v/v/v) is added and reacted at room temperature for 5 minutes. The support is washed with acetonitrile and then a solution of acetic anhydride/lutidine/THF (1:1:8, v/v/v), and N-methyl imidazole/THF is added to cap the unreacted 5'-hydroxyl groups. The product is washed with acetonitrile.

The carrier containing the compound is treated with 30% aqueous ammonium hydroxide solution for 24 hours at 65° C. The aqueous solution is filtered, concentrated under reduced pressure to give the T-T phosphodiester dimer.

D. Synthesis of 5'-TTTTTTT-3'- phosphorothioate heptamer

5'-O-DMT-thymidine (50 mg, 2 mmole) bonded to CPG through an ester linkage transferred to a glass reactor, and a $CH_2Cl_2$ solution of 2% dichloroacetic acid (v/v) is added to deprotect the 5'-hydroxyl group. The product is washed with acetonitrile. Then, a 0.2M solution of 5'-O-DMT-thymidine-3'-O-(4-cyano-2-butenyl N,N-diisopropylphosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8, v/v/v), and N-methyl imidazole/THF is added to cap the unreacted 5'-hydroxyl groups. The product is washed with acetonitrile.

This complete cycle is repeated five more times to get the completely protected thymidine heptamer. The carrier containing the compound is treated with 30% aqueous ammonium hydroxide solution for 90 minutes at room temperature. The aqueous solution is filtered and concentrated under reduced pressure to give the phosphorothioate heptamer of TTTTTTT.

E. Synthesis of 5'-d(GACT)-3'- phosphorothioate tetramer

5'-O-DMT-thymidine (50 mg, 2 mmole) bonded to CPG through an ester linkage is taken in a glass reactor, and a $CH_2Cl_2$ solution of 2% dichloroacetic acid (v/v) is added to deprotect the 5'-hydroxyl group. The product is washed with acetonitrile. Then, a 0.2M solution of 5'-O-DMT-thymidine-3'-O-(4-cyano-2-butenyl N,N-diisopropylphosphoramidite) in acetonitrile and a 0.4M solution of 1H-tetrazole in aceto-nitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8, v/v/v), and N-methyl imidazole/THF is added to cap the unreacted 5'-hydroxyl groups. The product is washed with acetonitrile.

A $CH_2Cl_2$ solution of 2% dichloroacetic acid (volume/volume) is added to deprotect the 5'-hydroxyl groups. The product is washed with acetonitrile. Then, a 0.2M solution of N4-benzoyl-5'-O-DMT-2'-deoxycytidine-3'-O-(4-cyano-2-butenyl N,N-diisopropylphosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8, V/V/V), and N-methyl imidazole/THF is added to cap the unreacted 5'-hydroxyl groups. The product is washed with acetonitrile.

A $CH_2Cl_2$ solution of 2% dichloroacetic acid (v/v) is added to deprotect the 5'-hydroxyl group. The product is washed with acetonitrile. Then, a 0.2M solution of N6-benzoyl-5'-O-DMT-2'-deoxyadenosine-3'-O-(4-cyano-2-butenyl N,N-diisopropylphosphoramidite) in anhydrous acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8, v/v/v), and N-methyl imidazole/THF is added to cap the unreacted 5'-hydroxyl groups. The product is washed with acetonitrile.

A dichloromethane solution of 2% dichloroacetic acid (volume/volume) is added to deprotect the 5'-hydroxyl group. The product is washed with acetonitrile. Then, a 0.2M solution of N2-isobutyryl-5'-O-DMT-2'-deoxyguanosine-3'-O-(4-cyano-2-butenyl N,N-diisopropylphosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

The carrier containing the compound is treated with 30% aqueous ammonium hydroxide solution for 90 minutes at room temperature and then incubated at 55° C. for 24 hour. The aqueous solution is filtered, concentrated under reduced pressure to give a phosphorothioate tetramer of 5'-dG-dA-dC-T-3'.

EXAMPLE 6

1-Trimethylsilylthioxy-4-cyano-2-butene

To a stirred mixture of 1-cyano-2,3-butadiene (0.1 mol) and trimethylsilylthiol (0.1 mol) in anhydrous ether (300 ml) under argon, is added a catalytic amount of rhodium acetate at room temperature. After 24 hours the reaction mixture is filtered and concentrated to give the title compound.

EXAMPLE 7

4-Cyano-2-butenyl-N,N,N',N'-tetraisopropylthiophosphorodiamidite

A 500 mL three-necked flask equipped with a magnetic stirrer, a glass stopper and an inlet for argon is assembled, after drying in an oven at 120° C. for 1 hour. The flask is purged with argon while cooling and an atmosphere of argon is maintained inside the flask. Anhydrous ether (150 mL) and phosphorous trichloride (67.5 mmol) is added to the flask. 1-Trimethylsilyl-4-cyano-2-butene (50 mmol) in ether (50 mL) is slowly added to the reaction flask with stirring at 0° C. (ice bath) using a pressure-equalized addition funnel. After the addition is complete, the ice bath is removed and the reaction is stirred for three hours at room temperature. The reaction mixture is then transferred to a 500 mL flask and concentrated under reduced pressure.

To the resulting residue in anhydrous ether (200 mL) is added diisopropylamine (57.7 mL) at 0° C. under argon. After the addition is complete, stirring is continued at room temperature for 16 hours. The reaction mixture is filtered and concentrated and the resulting residue purified by silica gel column chromatography to afford the title compound.

EXAMPLE 8

Preparation of protected phosphorothioamidite monomers
A. 5'-O-DMT-thymidine-3'-O-(4-cyano-2-butenyl N,N-diisopropylthiophosphoramidite)

A 250 mL two-necked flask equipped with a magnetic stirrer, a glass stopper and an inlet for argon is assembled, after drying in an oven at 120° C. for 1 hour. The flask is purged with argon while cooling and an atmosphere of argon is maintained inside the flask. 5'-O-DMT-thymidine (7 mmol) and 5-(4-nitrophenyl)1H-tetrazole (5.6 mmol) and anhydrous acetonitrile (50 mL) is added to the flask. To this stirred mixture at room temperature is added a solution of 4-cyano-2-butenyl-N,N,N',N'-tetraisopropylthiophosphorodiamidite (10.5 mmol) in acetonitrile (50 mL). After stirring for two hours, the reaction mixture is filtered and the filtrate diluted with ethyl acetate (100 mL), washed once with cold aqueous solution of saturated sodium bicarbonate, brine and dried (MgSO$_4$). The dried solution is filtered and the filtrate is concentrated under reduced pressure and purified by silica gel flash column chromatography to give the title compound.
B. N2-Isobutyryl-5'-O-DMT-2'-deoxyguanosine-3'-O-(4-cyano-2-butenyl N,N-diisopropylthiophosphoramidite)

A 250 mL two-necked flask equipped with a magnetic stirrer, a glass stopper and an inlet for argon is assembled, after drying in an oven at 120° C. for 1 hour. The flask is purged with argon while cooling and an atmosphere of argon is maintained inside the flask. The flask is charged with N2-isobutyryl-5'-O-DMT-2'-deoxyguanosine (5 mmol) and diisopropyl ammonium tetrazolide (4 mmol). Anhydrous acetonitrile (50 mL) is added. To this stirred mixture at room temperature is added a solution of 4-cyano-2-butenyl-N,N, N',N'-tetraisopropylthiophosphorodiamidite (7.5 mmol) in acetonitrile (50 mL). After stirring for two hours, the reaction mixture is filtered and the filtrate diluted with ethyl acetate (100 mL), washed once with cold saturated sodium bicarbonate solution, brine and dried (MgSO$_4$). The dried solution is filtered and the resulting filtrate is concentrated under reduced pressure. The resulting residue is purified by silica gel flash column chromatography to give the title compound.

C. N6-Benzoyl-5'-O-DMT-2'-deoxyadenosine-3'-O-(4-cyano-2-butenyl-N,N-diisopropylthiophosphoramidite)

A 250 mL two-necked flask equipped with a magnetic stirrer, a glass stopper and an inlet for argon is assembled, after drying in an oven at 120° C. for 1 hour. The flask is purged with argon while cooling and an atmosphere of argon is maintained inside the flask. The flask is charged with N6-benzoyl-5'-O-DMT-2'-deoxyadenosine (5 mmol) and diisopropylammonium tetrazolide (4 mmol). Anhydrous acetonitrile (50 mL) is added. To this stirred mixture at room temperature is added a solution of 4-cyano-2-butenyl-N,N, N',N'-tetraisopropylthiophosphorodiamidite (6 mmol) in acetonitrile (50 mL). After stirring for two hours, the reaction mixture is filtered and concentrated to a residue which is purified by silica gel flash column chromatography to give the title compound.
D. N4-Benzoyl-5'-O-DMT-2'-deoxycytidine-3'-O-(4-cyano-2-butenyl N,N-diisopropylthiophosphoramidite)

A 250 mL two-necked flask equipped with a magnetic stirrer, a glass stopper and an inlet for argon is assembled, after drying in an oven at 120° C. for 1 hour. The flask is purged with argon while cooling and an atmosphere of argon is maintained inside the flask. The flask is charged with N4-benzoyl-5'-O-DMT-2'-deoxycytidine (5 mmol) and diisopropylammonium tetrazolide (4 mmol). Anhydrous acetonitrile (50 mL) is added. To this stirred mixture at room temperature is added a solution of 4-cyano-2-butenyl-N,N, N',N'-tetraisopropylthiophosphorodiamidite (7.5 mmol) in acetonitrile (50 mL). After stirring for two hours, the reaction mixture is filtered and the filtrate diluted with ethyl acetate (100 mL), washed once with cold saturated sodium bicarbonate solution and then brine. The organic layer is dried (MgSO$_4$), filtered, and the filtrate concentrated under reduced pressure. The resulting residue is purified by silica gel flash column chromatography to give the title compound.

EXAMPLE 9

Coupling Procedures
A. Synthesis of T-T phosphorodithioate dimer 100 milligram (4 mmole) of 5'-O-DMT-thymidine bonded to CPG (controlled pore glass) through an ester linkage (commercially available) is transferred to a glass reactor, and a dichloromethane solution of 2% dichloroacetic acid (volume/volume) is added to deprotect the 5'-hydroxyl group. The product is washed with dichloromethane and then with acetonitrile. A 0.2M solution of 5'-O-DMT-thymidine-3'-O-(4-cyano-2-butenyl N,N-diisopropylthiophosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/ THF (1:1:8), and N-methyl imidazole/THF is added to cap any unreacted 5'-hydroxyl groups. The product is washed with acetonitrile.

The CPG containing the compound is treated with 30% aqueous ammonium hydroxide solution for 24 hours at 65° C. The aqueous solution is filtered, concentrated under reduced pressure to give the phosphorodithioate T-T dimer.
B. Synthesis of C-T phosphorodithioate dimer 5'-O-DMT-thymidine (100 mg, 4 mmole) bonded to CPG through an ester linkage is transferred to a glass reactor, and a CH$_2$Cl$_2$ solution of 2% dichloroacetic acid (v/v) is added to deprotect the 5'-hydroxyl groups. The product is washed with acetonitrile. Then, a 0.2M solution of N4-benzoyl-5'-O-DMT-2'-deoxycytidine-3'-O-(4-cyano-2-butenyl N,N-diisopropylthiophosphoramidite) in acetonitrile and a 0.4M solution of 1H-tetrazole in acetonitrile is added, and reacted at room temperature for 5 minutes. The product is washed with acetonitrile and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl groups. The product is washed with acetonitrile.

The carrier containing the compound is treated with 30% aqueous ammonium hydroxide solution for 24 hours at 65° C. The aqueous solution is filtered, concentrated under reduced pressure to give the phosphorodithioate dimer of dC-T.

C. Synthesis of T-T phosphorothioate dimer

5'-O-DMT-thymidine (100 mg, 4 mmole) bonded to CPG through an ester linkage is transferred to a glass reactor, and a $CH_2Cl_2$ solution of 2% dichloroacetic acid (v/v) is added to deprotect the 5'-hydroxyl group. The product is washed with $CH_2Cl_2$ and then with acetonitrile. A 0.2M solution of 5'-O-DMT-thymidine-3'-O-(4-cyano-2-butenyl N,N-diisopropylthiophosphoramidite) in acetonitrile and a 0.4M solution of 1H-tetrazole in acetonitrile is added, and reacted at room temperature for 5 minutes. The product is washed with acetonitrile, and then 0.1M iodine in water/pyridine/THF (2:20:80, v/v/v) is added and reacted at room temperature for 5 minutes. The support is washed with acetonitrile and then a solution of acetic anhydride/lutidine/THF (1:1:8, v/v/v), and N-methyl imidazole/THF is added to cap the unreacted 5'-hydroxyl groups. The product is washed with acetonitrile.

The CPG containing the compound is treated with 30% aqueous ammonium hydroxide solution for 24 hours at 65° C. The aqueous solution is filtered, concentrated under reduced pressure to give the T-T phosphorothioate dimer.

D. Synthesis of 5'-TTTTTTT-3' phosphorodithioate heptamer

5'-O-DMT-thymidine (50 mg, 2 mmole) bonded to CPG through an ester linkage is transferred to a glass reactor, and a $CH_2Cl_2$ solution of 2% dichloroacetic acid (v/v) is added to deprotect the 5'-hydroxyl groups. The product is washed with acetonitrile. Then, a 0.2M solution of 5'-O-DMT-thymidine-3'-O-(4-cyano-2-butenyl N,N-diisopropylthiophosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8, v/v/v), and N-methyl imidazole/THF is added to cap the unreacted 5'-hydroxyl groups. The product is washed with acetonitrile.

This complete cycle is repeated five more times to get the completely protected thymidine heptamer. The carrier containing the compound is treated with 30% aqueous ammonium hydroxide solution for 90 minutes at room temperature. The aqueous solution is filtered and concentrated under reduced pressure to give the phosphorothioate heptamer of TTTTTTT.

E. Synthesis of 5'-d(GACT)-3' phosphorodithioate tetramer

5'-O-DMT-thymidine (50 mg, 2 mmole) bonded to CPG through an ester linkage is taken in a glass reactor, and a $CH_2Cl_2$ solution of 2% dichloroacetic acid (v/v) is added to deprotect the 5'-hydroxyl group. The product is washed with acetonitrile. Then, a 0.2M solution of 5'-O-DMT-thymidine-3'-O-(4-cyano-2-butenyl N,N-diisopropylthiophosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8, v/v/v), and N-methyl imidazole/THF is added to cap the unreacted 5'-hydroxyl groups. The product is washed with acetonitrile.

A $CH_2Cl_2$ solution of 2% dichloroacetic acid (volume/volume) is added to deprotect the 5'-hydroxyl groups. The product is washed with acetonitrile. Then, a 0.2M solution of N4-benzoyl-5'-O-DMT-2'-deoxycytidine-3'-O-(4-cyano-2-butenyl N,N-diisopropylthiophosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8, V/V/V), and N-methyl imidazole/THF is added to cap the unreacted 5'-hydroxyl groups. The product is washed with acetonitrile.

A $CH_2Cl_2$ solution of 2% dichloroacetic acid (v/v) is added to deprotect the 5'-hydroxyl group. The product is washed with acetonitrile. Then, a 0.2M solution of N6-benzoyl-5'-O-DMT-2'-deoxyadenosine-3'-O-(4-cyano-2-butenyl N,N-diisopropylthiophosphoramidite) in anhydrous acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8, v/v/v), and N-methyl imidazole/THF is added to cap the unreacted 5'-hydroxyl groups. The product is washed with acetonitrile.

A dichloromethane solution of 2% dichloroacetic acid (volume/volume) is added to deprotect the 5'-hydroxyl group. The product is washed with acetonitrile. Then, a 0.2M solution of N2-isobutyryl-5'-O-DMT-2'-deoxyguanosine-3'-O-(4-cyano-2-butenyl N,N-diisopropylthiophosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

The carrier containing the compound is treated with 30% aqueous ammonium hydroxide solution for 24 hours at 65° C. The aqueous solution is filtered, concentrated under reduced pressure to give a phosphorothioate tetramer of 5'-dG-dA-dC-T-3'.

EXAMPLE 10

Standard Deprotection Procedures

A. Deprotection using NH$_4$OH

A homothymidine phosphorothioate dodecamer was synthesized as per the procedures of Example 5(D). The dodecamer was treated with saturated NH$_4$OH for 24 hours at 65° C. to afford the completely deprotected product as determined by mass spectroscopy.

B. Deprotection using CH$_3$NH$_2$

A homothymidine phosphorothioate dodecamer was synthesized as per the procedures of Example 5(D). The dodecamer was treated with CH$_3$NH$_2$ at 55° C. to afford the completely deprotected product as determined by mass spectroscopy.

EXAMPLE 11

Synthesis of a Phosphorothioate Homo T 20 mer

5'-O-DMT-thymidine bonded to CPG (controlled pore glass) through an ester linkage (commercially available) is transferred to a glass reactor. The CPG bound 5'-O-DMT-thymidine was washed with acetonitrile for 30 seconds followed by dichloromethane for 30 seconds. The CPG bound 5'-O-DMT-thymidine was treated with dichloroacetic acid (3%) in dichloromethane for 2 minutes followed by washing with acetonitrile for 3 minutes.

The resulting detritylated thymidine bonded to CPG was reacted simultaneously with equal volumes of 5'-O-DMT-thymidine-3'-O-(4-cyano-2-butenyl N,N-diisopropylphosphoramidite) (0.2M) in acetonitrile and 1H-tetrazole (0.4M) in acetonitrile at room temperature for 5 minutes. The reagents are drained away and this step was repeated for an additional 5 minutes. The resulting T-T dimer bonded to CPG was washed with acetonitrile for 30 seconds and oxidized with Beaucage reagent (0.5M) in acetonitrile for 3 minutes. This sulfurization step was repeated for an additional 3 minutes. The CPG was washed with acetonitrile for 30 seconds followed by treatment with equal volumes of acetic anhydride/lutidine/THF (1:1:8), and N-methyl imidazole/THF for 1 minute to cap any unreacted sites. The above process of washing, detritylating, reacting with a monomer subunit, oxidizing and capping was repeated 18 times to synthesize the 20 mer homo thymidine phosphorothioate oligomeric compound.

The CPG bound 20 mer was treated with 30% aqueous ammonium hydroxide solution for 2 hours at room temperature. The aqueous solution was filtered, concentrated under reduced pressure to give the phosphorothioate homo T 20 mer.

The synthesis was run on a 1 μmole scale and the overall coupling efficiency was found to be greater than 99% as determined by spectrophotometric quantitation of released p,p'-dimethoxytriphenylmethyl cation.

EXAMPLE 12

Synthesis of a Phosphorothioate Mixed Sequence 20 mer (GCC-CAA-GCT-GGC-ATC-CGT-CA)

Following the procedures of Example 11, the mixed sequence 20 mer (GCC-CAA-GCT-GGC-ATC-CGT-CA) was synthesized using the protected monomer subunits of Example 4 (a,b,c, and d), 5'-O-DMT-thymidine-3'-O-(4-cyano-2-butenyl N,N-diisopropylphosphoramidite), N2-isobutyryl-5'-O-DMT-2'-deoxyguanosine-3'-O-(4-cyano-2-butenyl N,N-diisopropylphosphoramidite), N6-benzoyl-5'-O-DMT-2'-deoxyadenosine-3'-O-(4-cyano-2-butenyl N,N-diisopropylphosphoramidite), N4-Benzoyl-5'-O-DMT-2'-deoxycytidine-3'-O-(4-cyano-2-butenyl N,N-diisopropylphosphoramidite).

The synthesis was carried out on a 1 μmole scale and the 20 mer was deprotected with aqueous NH$_4$OH at room temperature for 1 hour followed by heating to 60° C. for 20 hours. The crude oligomer was purified by reverse-phase HPLC. The product was further characterized by capillary gel electrophoresis.

EXAMPLE 13

Synthesis of a Silyl-containing Nucleosides

The synthesis of representative silyl-containing nucleosides of the invention is depicted below in Scheme 3:

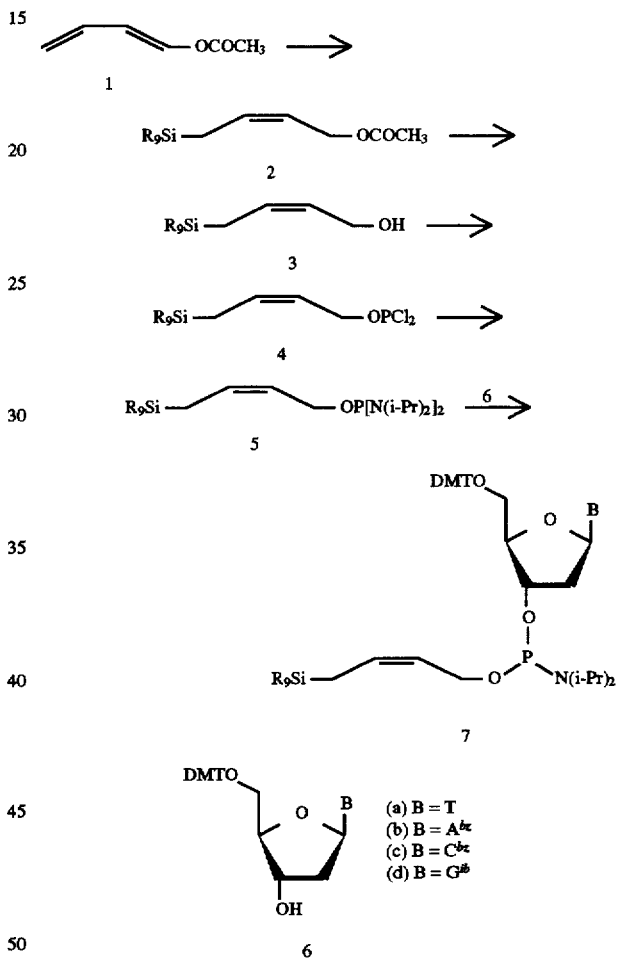

Commercially available 1-acetoxy-1,3-butadiene (compound 1) is first reacted with (R$_9$)$_3$Si—H in the presence of Rh$_2$Cl$_2$(CO)$_4$ to produce compound 2. The hydroxyl group is deprotected using K$_2$CO$_3$ in methanol to produce compound 3. Compound 3 is then reacted with PCl$_3$ in ether at 0° C. to produce compound 4, which is further reacted with isopropylamine in ether to produce compound 5. Compound 5 is then reacted with a 5'-DMT nucleoside 6 in the presence of tetrazole in CH$_2$Cl$_2$ at room temperature to yield synthon 7.

EXAMPLE 14

Preparation of 1,1,1-triphenyl-4-acetoxy-1-sila-2-butene

A solution of 1-acetoxy-1,3-butadiene (0.1 mol), triphenylsilane (0.1 mol), and Rh$_2$Cl$_2$(CO)$_4$ (194.5 mg, 0.625 mol) in 100 mL of toluene was stirred at room temperature under argon for 3 days. The reaction mixture is treated with decolorizing charcoal, and the mixture boiled briefly. After cooling, the reaction mixture is filtered through Celite. Concentration of the solution will afford the title compound.

EXAMPLE 15

Preparation of 1,1,1-triphenyl-1-sila-2-butene-4-ol

The crude acetoxy compound from Example 14 is dissolved in 250 mL methanol, and 25.0 g of potassium carbonate is added all at once. After stirring for 2 hours, the reaction mixture is filtered and concentrated. The concentrated residue is partitioned between 200/200 mL water/ethyl acetate. The organic layer is removed, washed with brine, dried and concentrated. The crude material is purified by flash chromatography using silica gel to afford the pure product.

EXAMPLE 16

Preparation of 1,1,1-triphenyl-1-sila-2-butenyl-N,N-diisopropylbisphosphoramidite A 500 mL three-necked flask equipped with a magnetic stirrer, a glass stopper and an inlet for argon is assembled under argon atmosphere. All glassware are dried in an oven at 120° C. for 1 hour. The reaction flask is charged with anhydrous ether (150 mL) and phosphorous trichloride (67.5 mmol). 1,1,1-triphenyl-1-sila-2-butene-4-ol (50 mmol) in ether (50 mL) is added to the reaction flask slowly with stirring at 0° C. (ice cooling) using pressure-equalized addition funnel. After addition is complete, ice bath is removed and the reaction is stirred for three hours. The reaction mixture then is transferred to a 500 mL flask and concentrated under reduced pressure.

To this product in anhydrous ether (200 mL) is added diisopropylamine (57.7 mL) at 0° C. under argon. After the addition is complete, stirring is continued at room temperature for 16 hours (overnight). The reaction mixture is filtered and concentrated to afford the title compound.

EXAMPLE 17

Preparation of Protected Phosphoramidite Monomers
A. 5'-O-(4,4'-dimethoxytrityl)thymidine-3'-O-(1,1,1-triphenyl-1-sila-2-butenyl-N,N-diisopropylphosphoramidite).

A 250 mL two-necked flask equipped with a magnetic stirrer, a gas inlet for argon, and a septum is assembled under an argon atmosphere. All glassware are dried at 120° C. for 1 hour. The flask is charged with 5'-O-(4,4'-dimethoxytrityl)thymidine (7 mmol) and 5-(4-nitrophenyl)1H-tetrazole (5.6 mmol). Anhydrous acetonitrile (50 mL) is added. To this stirred mixture under argon at room temperature is added a solution of 1,1,1-triphenyl-1-sila-2-butenyl N,N-diisopropylphosphoramidite (10.5 mmol) in acetonitrile (50 mL). After stirring for two hours, the reaction mixture is filtered and the filtrate diluted with ethyl acetate (100 mL), washed once with cold saturated sodium bicarbonate solution, brine and dried (MgSO$_4$). The dried solution is concentrated under reduced pressure to afford a viscous foamy liquid. The crude product is purified by flash chromatography using silica gel to afford the product. Triethylamine (1%) is used throughout the purification.

B. N$^2$-Isobutyryl-5'-O-(4,4'-dimethoxytrityl)-2'-deoxyguanosine-3'- O-(1,1,1-triphenyl-1-sila-2-butenyl-N,N-diisopropylphosphoramidite).

A 250 mL two-necked flask equipped with a magnetic stirrer, a gas inlet for argon, and a septum is assembled under an argon atmosphere. All glassware are dried at 120° C. for 1 hour. The flask is charged with N2-Isobutyryl-5'-O-(4,4'-dimethoxytrityl)-2'-deoxyguanosine (5 mmol) and diisopropyl ammonium tetrazolide (4 mmol). Anhydrous acetonitrile (50 mL) is added. To this stirred mixture under argon at room temperature is added a solution of 1,1,1-triphenyl-1-sila-2-butenyl-N,N-diisopropylphosphoramidite (7.5 mmol) in acetonitrile (50 mL). After stirring for two hours, the reaction mixture is filtered and the filtrate diluted with ethyl acetate (100 mL), washed once with cold saturated sodium bicarbonate solution, brine and dried (MgSO$_4$). The dried solution is concentrated under reduced pressure to afford the product which is purified by flash chromatography using silica gel. Triethylamine (1%) is used throughout the purification.

C. N$^6$-Benzoyl-5'-O-(4,4'-dimethoxytrityl)-2'-deoxyadenosine-3'-O-(1,1,1-triphenyl-1-sila-2-butenyl-N,N-diisopropylphosphoramidite).

A 250 mL two-necked flask equipped with a magnetic stirrer, a gas inlet for argon, and a septum is assembled under an argon atmosphere. All glassware are dried at 120° C. for 1 hour. The flask is charged with N$^6$-benzoyl-5'-O-(4,4'-dimethoxytrityl)-2'-deoxyadenosine (5 mmol) and diisopropylammonium tetrazolide (4 mmol). Anhydrous acetonitrile (50 mL) is added. To this stirred mixture under argon at room temperature is added a solution of 1,1,1-triphenyl-1-sila-2-butenyl-N,N-diisopropylphosphoramidite (6 mmol) in acetonitrile (50 mL). After stirring for two hours, the reaction mixture is filtered and concentrated to afford the product which is purified by flash chromatography using silica gel. Triethylamine (1%) is used throughout the purification.

D. N$^4$-Benzoyl-5'-O-(4,4,-dimethoxytrityl)-2'-deoxycytidine-3'-O-(1,1,1-triphenyl-1-sila-2-butenyl-N,N-diisopropylphosphoramidite)

A 250 mL two-necked flask equipped with a magnetic stirrer, a gas inlet for argon, and a septum is assembled under an argon atmosphere. All glassware are dried at 120° C. for 1 hour. The flask is charged with N4-benzoyl-5'-O-(4,4'-dimethoxytrityl)-2'-deoxycytidine (5 mmol) and diisopropylammonium tetrazolide (4 mmol). Anhydrous acetonitrile (50 mL) is added. To this stirred mixture under argon at room temperature is added a solution of 1,1,1-triphenyl-1-sila-2-butenyl N,N-diisopropylphosphoramidite (7.5 mmol) in acetonitrile (50 mL). After stirring for two hours, the reaction mixture is filtered and the filtrate diluted with ethyl acetate (100 mL), washed once with cold saturated sodium bicarbonate solution, brine and dried (MgSO$_4$). The dried solution is concentrated under reduced pressure to afford the product which is purified by flash chromatography using silica gel. Triethylamine (1%) is used throughout the purification.

EXAMPLE 18

Coupling Procedures
A. Synthesis of T-T phosphorothioate dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. Then, a 0.2M solution of 5'-O-(4,4'-dimethoxytrityl)thymidine-3'-O-(1,1,1-triphenyl-1-sila-2-butenyl-N,N-diisopropylphosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/ lutidine/THF (1:1:8), and N-methyl imidazole/THF is added to cap the unreacted 5'-hydroxyl group. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure and then treated at room temperature with 1.0M solution of tetra-n-butyl ammonium fluoride in THF to give a phosphorothioate dimer of T-T.

B. Synthesis of C-T phosphorothioate dimer 100 milligram (4 mmole) of 5'-O-Dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with acetonitrile. Then, a 0.2M solution of N4-Benzoyl-5'-O-(4,4'-dimethoxytrityl)-2'-deoxycytidine-3'-O-(1,1,1-triphenyl-1-sila-2-butenyl-N,N-diisopropylphosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/ THF (1:1:8), and N-methyl imidazole/THF is added to cap the unreacted 5'-hydroxyl group. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure and then treated at room temperature with 1.0M solution of tetra-n-butyl ammonium fluoride in THF to give a phosphorothioate dimer of dC-T.

D. Synthesis of 5'-TTTTTTT-3' phosphorothioate heptamer 50 milligram (2 mole) of 5'-O-Dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with acetonitrile. Then, a 0.2M solution of 5'-O-(4,4'-dimethoxytrityl)thymidine-3'-O-(1,1,1-triphenyl-1-sila-2-butenyl-N,N-diisopropylphosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride lutidine/THF (1:1:8), and N-methyl imidazole/THF is added to cap the unreacted 5'-hydroxyl group. The product is washed with acetonitrile.

This complete cycle is repeated five more times to get the completely protected thymidine heptamer. The carrier containing the compound is treated with 30% aqueous ammonium hydroxide solution for 90 minutes at room temperature. The aqueous solution is filtered, concentrated under reduced pressure to give a phosphorothioate heptamer of TTTTTTT.

E. Synthesis of 5'-d(GACT)-3' phosphorothioate tetramer 50 milligram (2 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with acetonitrile. Then, a 0.2M solution of 5'-O-(4,4'-dimethoxytrityl)thymidine-3'-O-(1,1,1-triphenyl-1-sila-2-butenyl-N,N-diisopropylphosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/ THF (1:1:8), and N-methyl imidazole/THF is added to cap the unreacted 5'-hydroxyl group. The product is washed with acetonitrile.

A dichloromethane solution of 2% dichloroacetic acid (volume/volume) is added to deprotect the 5'-hydroxyl group. The product is washed with acetonitrile. Then, a 0.2M solution of N4-benzoyl-5'-O-(4,4'-dimethoxytrityl)-2'-deoxycytidine-3'-O-(1,1,1-triphenyl-1-sila-2-butenyl-N,N-diisopropylphosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/ THF (1:1:8), and N-methyl imidazole/THF is added to cap the unreacted 5'-hydroxyl group. The product is washed with acetonitrile.

A dichloromethane solution of 2% dichloroacetic acid (volume/volume) is added to deprotect the 5'-hydroxyl group. The product is washed with acetonitrile. Then, a 0.2M solution of N6-benzoyl-5'-O-(4,4'-dimethoxytrityl)-2'-deoxyadenosine-3'-O-(1,1,1-triphenyl-1-sila-2-butenyl-N,N-diisopropylphosphoramidite) in anhydrous acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/ lutidine/THF (1:1:8), and N-methyl imidazole/THF is added to cap the unreacted 5'-hydroxyl group. The product is washed with acetonitrile.

A dichloromethane solution of 2% dichloroacetic acid (volume/volume) is added to deprotect the 5'-hydroxyl group. The product is washed with acetonitrile. Then, a 0.2M solution of N2-isobutyryl-5'-O-(4,4'-dimethoxytrityl) 2'-deoxyguanosine-3'-O-(1,1,1-triphenyl-1-sila-2-butenyl-N,N-diisopropylphosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/ THF (1:1:8), and N-methyl imidazole/THF is added to cap the unreacted 5'-hydroxyl group. The product is washed with acetonitrile.

The carrier containing the compound is treated with 30% aqueous ammonium hydroxide solution for 90 minutes at room temperature and then incubated at 55° C. for 24 hours. The aqueous solution is filtered, concentrated under reduced pressure to give a phosphorothioate tetramer of 5'-dG-dA-dC-T-3'.

EXAMPLE 19

3'-O-Levulinylthymidine

The title compound was synthesized according a published procedure, see G. Kumar, M. S. Poonian, *J. Org. Chem.* 1984, 49, 4905–4912.

EXAMPLE 20

3'-O-Levulinyl—N2-isobutyryl-2'-deoxyguanosine

5'-DMT-N2-isobutyryl-2'-deoxyguanosine (71.6 g, 0.112 mol) is transferred to a 1000 ml flask and anhydrous dioxane (700 ml) is added and stirred until the solution becomes homogeneous. Then dicyclohexylcarbodiimide (57.8 g, 0.280 mol), levulinic acid (25.9 g, 0.224 mol) and 4-dimethylaminopyridine (0.56 g) are added and vigorously stirred using magnetic stirring. After 3 hours, the reaction mixture is filtered, the solid residue washed with ethyl acetate (250 ml). The filterates are combined and concentrated to afford a product.

This product is dissolved in dichloromethane (400 ml) and 2.5% DCA in dichloromethane (160 ml) is added and stirred. After 1 hour, the reaction mixture is diluted with dichloromethane (400 ml) and washed with saturated sodium bicarbonate solution. The organic layer is separated, dried and concentrated. The crude product is purified by flash chromatography using silica gel to give the title compound.

EXAMPLE 21

Synthesis of T-T phosphorothioate dimer

To a stirred solution of 3'-O-levulinylthymidine (5 mole) and 1H-tetrazole (5 mole) in anhydrous acetonitrile (25 ml) at room temperature under argon is added a solution of 5'-O-(4,4'-dimethoxytrityl)thymidine-3'-O-(4-diphenylmethylsilyl-2-butenyl N,N-diisopropyl phosphoramidite) (6 mole) in acetonitrile (20 ml). After stirring for 3 h, the sulfurizing reagent (a mixture of sulfur (200 mmole)/triethylamine (20 mole) in dichloromethane (75 ml) is added all at once. After 5 hours, the reaction mixture is filtered and concentrated. The crude product is purified by flash chromatography using silica gel and ethylacetate/hexane as eluents.

EXAMPLE 22

Deprotection of 3'-O-levulinyl group

5'-(O-4,4'-Dimethoxytrityl)-3'-(O-levulinyl)-thymidine dimer (35.0 g) is dissolved in an ice-cold solution of hydrazine-hydrate (10.0 g), pyridine (240 ml) and acetic acid (240 ml). After 10 minutes, ice is added, followed by extraction with dichloromethane. The organic phase is dried over sodium sulfate, filtered and the solvent is removed. The residue is purified by silica gel column chromatography (ethyl acetate/n-hexanes 1:1, then ethyl acetate, 0.1% triethylamine) to afford the desired product.

EXAMPLE 23

Synthesis of thymidyl-thymidine dimer amidite

Under argon, a solution of 1H tetrazole (5 mmol) and 4-cyano-2-butenyl-N,N,N',N'-tetraisopropylphosphorodiamidite (30 mmol) in dry acetonitrile (100 ml) is added to thymidyl-thymidine dimer (20 mmol). After 2 hours, ethyl acetate is added and the solution is extracted with aqueous sodium bicarbonate. The organic phase is dried over sodium sulfate and the solvent is removed under reduced pressure. The residue is purified by column chromatography to afford the desired product.

EXAMPLE 24

Synthesis of C-T-phosphorothioate dimer

To a stirred solution of 3'-O-levulinylthymidine (5 mmole) and 1H-tetrazole (5 mmole) in anhydrous acetonitrile (25 ml) at room temperature under argon is added a solution of 5'-O-(4,4'-dimethoxytrityl)-2'-deoxycytidine-3'-O-(4-diphenylmethylsilyl-2-butenyl N,N-diisopropyl phosphoramidite) (6 mmole) in acetonitrile (20 ml). After stirring for 3 h, the sulfurizing reagent (a mixture of sulfur (200 mmole)/triethylamine (20 mole) in dichloromethane (75 ml) is added all at once. After 5 hours, the reaction mixture is filtered and concentrated. The crude product is purified by flash chromatography using silica gel and ethylacetate/hexane as eluents.

EXAMPLE 25

Deprotection of 3'-O-levulinyl group

5'-(O-4,4'-Dimethoxytrityl)-3'-(O-levulinyl)-2'-deoxycytidinyl-thymidine dimer (35.0 g) is dissolved in an ice-cold solution of hydrazine-hydrate (10.0 g), pyridine (240 ml) and acetic acid (240 ml). After 10 minutes, ice is added, followed by extraction with dichloromethane. The organic phase is dried over sodium sulfate, filtered and the solvent is removed. The residue is purified by silica gel column chromatography (ethyl acetate/n-hexanes 1:1, then ethyl acetate, 0.1% triethylamine) to afford the desired product.

EXAMPLE 26

Synthesis of 2'-deoxycytidinyl-thymidine dimer amidite

Under argon, a solution of 1H tetrazole (5 mmol) and 4-cyano-2-butenyl-N,N,N',N'-tetraisopropylphosphorodiamidite (30 mmol) in dry acetonitrile (100 ml) is added to 2'-deoxycytidinyl-thymidine dimer (20 mmol). After 2 hours, ethyl acetate is added and the solution is extracted with aqueous sodium bicarbonate. The organic phase is dried over sodium sulfate and the solvent is removed under reduced pressure. The residue is purified by column chromatography to afford the desired product.

EXAMPLE 27

Synthesis of d(A-G)-phosphorothioate dimer

To a stirred solution of 3'-O-levulinyl-2'-deoxyguanosine (5 mole) and 1H-tetrazole (5 mole) in anhydrous acetonitrile (25 ml) at room temperature under argon is added a solution of 5'-O-(4,4'-dimethoxytrityl)-2'-deoxyadenosine-3'-O-(4-diphenylmethylsilyl-2-butenyl N,N-diisopropyl phosphoramidite) (6 mole) in acetonitrile (20 ml). After stirring for 3 h, the sulfurizing reagent (a mixture of sulfur (200 mmole)/triethylamine (20 mmole) in dichloromethane (75 ml) is added all at once. After 5 hours, the reaction mixture is filtered and concentrated. The crude product is purified by flash chromatography using silica gel and ethyl acetate/hexane as eluents.

EXAMPLE 28

Deprotection of 3'-O-levulinyl group

5'-(O-4,4'-Dimethoxytrityl)-3'-(O-levulinyl)-2'-deoxyadenosinyl-2'-deoxyguanosine dimer (35 g) is dissolved in an ice-cold solution of hydrazine-hydrate (10.0 g), pyridine (240 ml) and acetic acid (240 ml). After 10 minutes, ice is added, followed by extraction with dichloromethane. The organic phase is dried over sodium sulfate, filtered and the solvent is removed. The residue is purified by silica gel column chromatography (ethyl acetate/n-hexanes 1:1, then ethyl acetate, 0.1% triethylamine) to afford the desired product.

EXAMPLE 29

Synthesis of 2'-deoxyadenosinyl-2'-deoxyguanosine dimer amidite

Under argon, a solution of 1H tetrazole (5 mmol) and 4-cyano-2-butenyl-N,N,N',N'-tetraisopropylphosphorodiamidite (30 mmol) in dry acetonitrile (100 ml) is added to 2'-deoxyadenosinyl-2'-deoxyguanosine dimer (20 mmol). After 2 hours, ethyl acetate is added and the solution is extracted with aqueous sodium bicarbonate. The organic phase is dried over sodium sulfate and the solvent is removed under reduced pressure. The residue is purified by column chromatography to afford the desired product.

EXAMPLE 30

Synthesis of 5'-TTTTTTT-3' phosphorothioate heptamer 50 milligram (2 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with acetonitrile. Then, a 0.2M solution of 5'-O-(4,4'-dimethoxytrityl)-thymidyl-thymidine-3'-O-(4-cyano-2-butenyl N,N-diisopropylphosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

This complete cycle is repeated two more times to get the completely protected thymidine heptamer. The carrier containing the compound is treated with 30% aqueous ammonium hydroxide solution for 90 minutes at room temperature and then incubated at 55° C. for 1 hour. The aqueous solution is filtered, concentrated under reduced pressure to give a phosphorothioate heptamer of 5'-TTTTTTT-3'.

EXAMPLE 31

Synthesis of 5'-d(TTCTAGT)-3' phosphorothioate heptamer 50 milligram (2 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with acetonitrile. Then, a 0.2M solution of 5'-O-(4,4'-dimethoxytrityl)-2'-deoxyadenosinyl-2'-deoxyguanosine-3'-O-(4-cyano-2-butenyl N,N-diisopropylphosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

A dichloromethane solution of 2% dichloroacetic acid (volume/volume) is added to deprotect the 5'-hydroxyl group. The product is washed with acetonitrile. Then, a 0.2M solution of 5'-O-(4,4'-dimethoxytrityl)-2'-deoxycytidinyl-thymidine-3'-O-(4-cyano-2-butenyl N,N-diisopropylphosphoramidite) in acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

A dichloromethane solution of 2% dichloroacetic acid (volume/volume) is added to deprotect the 5'-hydroxyl group. The product is washed with acetonitrile. Then, a 0.2M solution of 5'-O-(4,4'-dimethoxytrityl)-thymidyl-thymidine-3'-O-(4-cyano-2-butenyl N,N-diisopropylphosphoramidite) in anhydrous acetonitrile and a 0.4M solution of 1H-tetrazole in acetonitrile is added, and reacted at room temperature for 5 minutes. The product is washed with acetonitrile, and then a 0.05M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

The carrier containing the compound is treated with 30% aqueous ammonium hydroxide solution for 90 minutes at room temperature and then incubated at 55° C. for 24 hour. The aqueous solution is filtered, concentrated under reduced pressure to give a phosphorothioate heptamer of 5'-d (TTCTAGT)-3'.

It is intended that each of the patents, publications, and other published documents mentioned or referred to in this specification be herein incorporated by reference in its entirety.

What is claimed is:

1. A compound having the Formula VII:

A—X₁—CH₂—CH=CH—CH₂—Z          VII wherein:

$X_1$ is O or S;

A is $(R_7)(R_8)P$—;

$R_8$ is $R_5$, or has the Formula X:

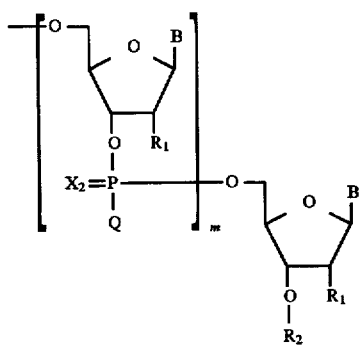

wherein:

each $R_1$, is, independently, H, —OH, —F, —O—$X_3$—D;

$X_3$ is alkyl having from 1 to 10 carbons;

D is H, amino, protected amino, alkyl substituted amino, imidazole, or (—O—$X_3$)$_p$, where p is 1 to about 10;

each $X_2$ is O or S;

$R_5$ is —N($R_6$)$_2$, or a heterocycloalkyl or heterocycloalkenyl ring containing from 4 to 7 atoms, and having up to 3 heteroatoms selected from the group consisting of nitrogen, sulfur, and oxygen;

each Q is —$X_1$H or —$X_1$—CH₂—CH=CH—CH₂—Z;

m is 0 to about 50;

each B, independently, is a naturally occurring or non-naturally occurring nucleobase or a protected naturally occurring or non-naturally occurring nucleobase; and $R_7$ is $R_5$, or has the Formula VIII:

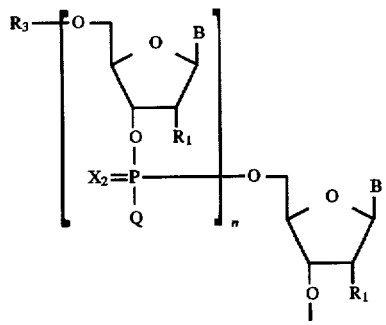

wherein:

$R_3$ is hydrogen, a hydroxyl protecting group, or a linker connected to a solid support; and n is 0 to about 50; with the proviso that the sum of m and n do not exceed 50; and Z is CN, halogen, NO₂, alkaryl, sulfoxyl, sulfonyl, thio, substituted sulfoxyl, substituted sulfonyl, or substituted thio, wherein the substituents are selected from the group consisting of alkyl, aryl, or alkaryl.

2. The compound of claim 1 wherein Z is CN.

3. The compound of claim 2 wherein $X_1$ is O.

4. The compound of claim 2 wherein $X_1$ is S.

5. The compound of claim 2 wherein A is H.

6. The compound of claim 2 wherein A is —P($R_5$)$_2$.

7. The compound of claim 5 wherein $R_5$ is —N(CH(CH₃)₂)₂.

8. The compound of claim 1 wherein $R_7$ has the Formula VIII.

9. The compound of claim 8 wherein n is 1 to 30.

10. The compound of claim 8 wherein n is 1 to about 25.

11. The compound of claim 8 wherein n is 0.

12. The compound of claim 2 wherein Z is CN; $X_1$ is O; and A is H.

13. The compound of claim 2 wherein Z is CN; $X_1$ is S; and A is H.

14. The compound of claim 2 wherein Z is CN; $X_1$ is O; and each $R_6$ is isopropyl.

15. The compound of claim 2 wherein Z is CN; $X_1$ is S; and each $R_6$ is isopropyl.

16. The compound of claim 1 having the Formula IV:

IV

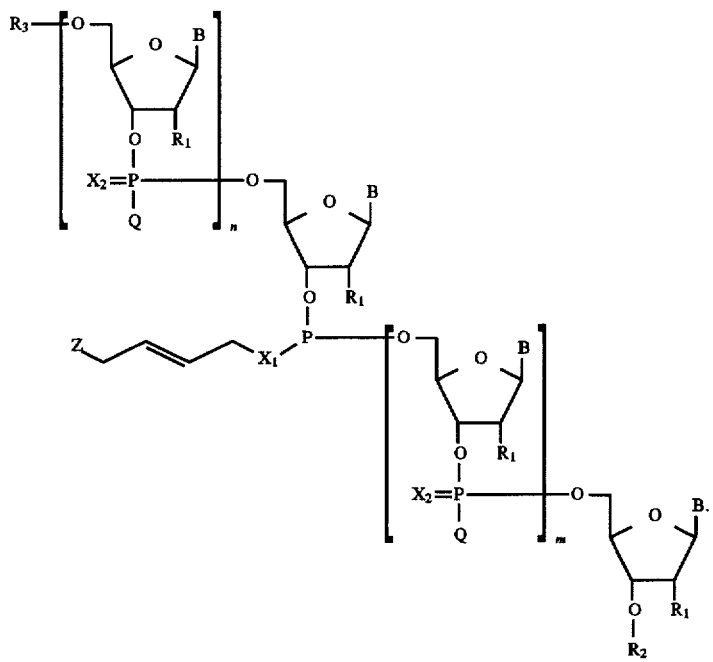

17. The compound of claim 16 wherein $R_2$ is a linker connected to a solid support.

18. The compound of claim 16 wherein $R_2$ is hydrogen.

19. The compound of claim 16 wherein m and n are each 0.

20. The compound of claim 16 wherein Z is CN; and $X_1$ is O.

21. A compound having the Formula:

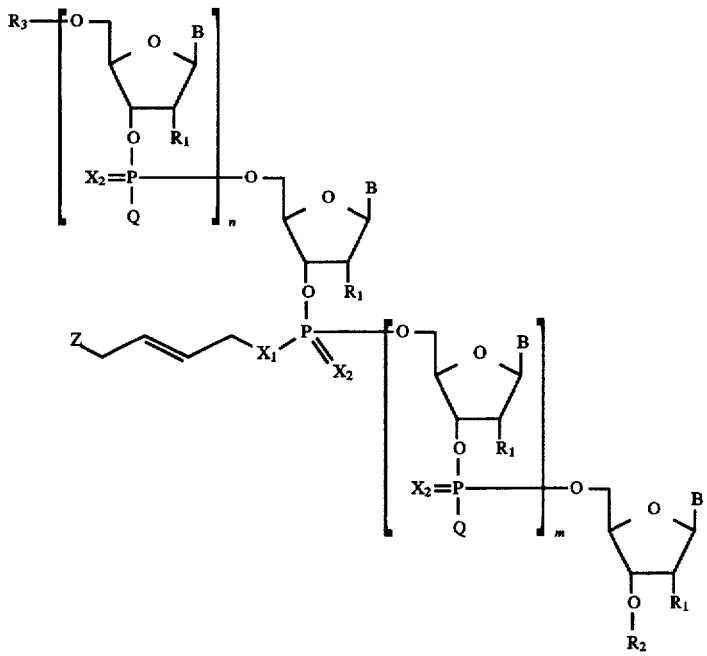

wherein:

each $R_1$, is, independently, H, —OH, —F, or —O—$X_3$—D;

D is H, amino, protected amino, alkyl substituted amino, imidazole, or (—O—$X_3$)$_p$, where p is 1 to about 10;

$R_2$ is a hydroxyl protecting group, or a linker connected to a solid support;

$R_3$ is hydrogen, a hydroxyl protecting group, or a linker connected to a solid support, provided that $R_2$ and $R_3$ are not both simultaneously a linker connected to a solid support;

$X_1$ is O or S;

each $X_2$ is O or S;

each $X_3$ is alkyl having from 1 to 10 carbons;

each Q is —$X_1$H or —$X_1$—$CH_2$—CH=CH—$CH_2$—Z;

m and n are each independently an integer from 0 to about 50, provided that the sum of m and n does not exceed 50;

each B, independently, is a naturally occurring or non-naturally occurring nucleobase or a protected naturally occurring or non-naturally occurring nucleobase; and Z is CN, halogen, $NO_2$, alkaryl, sulfoxyl, sulfonyl, thio, substituted sulfoxyl, substituted sulfonyl, or substituted thio, wherein the substituents are selected from the group consisting of alkyl, aryl, or alkaryl.

22. The compound of claim 21 wherein $R_2$ is a linker connected to a solid support.

23. The compound of claim 21 wherein $R_2$ is hydrogen.

24. The compound of claim 21 wherein m and n are each 0.

25. The compound of claim 21 wherein Z is CN; and $X_1$ is O.

26. The compound of claim 8 wherein $R_8$ is $R_5$.

27. The compound of claim 26 wherein n is from 2 to 50, and each Q has the Formula —$X_1$—$CH_2$—CH=CH—$CH_2$—Z.

28. An oligomeric compound comprising a moiety having the Formula IX;

$$\text{Z}\diagdown\diagup\diagdown\diagup X_1 \diagdown \underset{\underset{O-}{|}}{\overset{\overset{|}{O}}{P}} \quad \text{IX}$$

wherein:

Z is CN, halogen, $NO_2$, alkaryl, sulfoxyl, sulfonyl, thio, substituted sulfoxyl, substituted sulfonyl, or substituted thio, wherein the substituents are selected from the group consisting of alkyl, aryl, or alkaryl; and $X_1$ is O or S;

prepared by the steps of:

(a) providing a compound having the Formula II:

II wherein each $R_1$, is, independently, H, —OH, —F, or —O—$X_3$—D;

$X_3$ is alkyl having from 1 to 10 carbons;

D is H, amino, protected amino, alkyl substituted amino, imidazole, or (—O—$X_3$)$_p$, where p is 1 to about 10;

each $X_2$ is O or S;

$R_3$ is hydrogen, a hydroxyl protecting group, or a linker connected to a solid support:

each B, independently, is a naturally occurring or non-naturally occurring nucleobase or a protected naturally occurring or non-naturally occurring nucleobase;

n is 0 to about 50;

each Q is —$X_1$H or —$X_1$—$CH_2$—CH=CH—$CH_2$—Z;

$R_5$ is —N($R_6$)$_3$, or a heterocycloalkyl or heterocycloalkenyl ring containing from 4 to 7 atoms, and having up to 3 heteroatoms selected from the group consisting of nitrogen, sulfur, and oxygen;

$R_6$ is straight or branched chain alkyl having from 1 to 10 carbons;

(b) reacting the compound of Formula II with a compound having the Formula III:

III wherein $R_{3a}$ is hydrogen;

and $R_2$ is a hydroxyl protecting group, or a linker connected to a solid support;

(c) oxidizing the product of step (b) to form a further compound having the Formula III, wherein $R_{3a}$ is hydrogen, a hydroxyl protecting group, or a linker connected to a solid support.

* * * * *